(12) United States Patent
Khosrovaninejad et al.

(10) Patent No.: US 11,871,929 B2
(45) Date of Patent: Jan. 16, 2024

(54) COMPLEX SURGICAL DEVICE FOR CARRYING OUT AND PROTECTING AN ANASTOMOSIS

(71) Applicant: SafeHeal SAS, Paris (FR)

(72) Inventors: Charam Khosrovaninejad, Pernes les Fontaines (FR); Anne Osdoit, Paris (FR); Cécile Dupont, Paris (FR)

(73) Assignee: SafeHeal SAS, Paris (FR)

( * ) Notice: Subject to any disclaimer, the term of this patent is extended or adjusted under 35 U.S.C. 154(b) by 0 days.

(21) Appl. No.: 18/173,709

(22) Filed: Feb. 23, 2023

(65) Prior Publication Data

US 2023/0190272 A1    Jun. 22, 2023

Related U.S. Application Data

(63) Continuation of application No. 16/647,152, filed as application No. PCT/FR2018/052388 on Sep. 28, 2018, now Pat. No. 11,589,869.

(30) Foreign Application Priority Data

Oct. 19, 2017   (FR) ...................................... 1759847

(51) Int. Cl.
*A61B 17/11* (2006.01)
*A61F 2/966* (2013.01)
(Continued)

(52) U.S. Cl.
CPC ....... *A61B 17/1114* (2013.01); *A61B 17/1155* (2013.01); *A61F 2/966* (2013.01);
(Continued)

(58) Field of Classification Search
CPC ............. A61B 17/1114; A61B 17/1155; A61B 2017/1132; A61B 2217/005; A61F 2/966; A61F 2002/045; A61F 2/04
See application file for complete search history.

(56) References Cited

U.S. PATENT DOCUMENTS 3,799,172 A    3/1974  Szpur
3,885,567 A    5/1975  Ross
(Continued)

FOREIGN PATENT DOCUMENTS

CN    102387759 A    3/2012
CN    103370016 A   10/2013
(Continued)

OTHER PUBLICATIONS

Buhl S., et al., "Humidity Influence on the Adhesion of Biomimetic Fibrillar Surfaces", International Journal of Materials Research, 2009, vol. 100, No. 8, pp. 1119-1126.
(Continued)

*Primary Examiner* — Richard G Louis
(74) *Attorney, Agent, or Firm* — Eversheds Sutherland (US) LLP; Christopher C. Bolten; Albert K. Heng

(57) ABSTRACT

The present invention relates to a complex surgical device for carrying out an anastomosis in the intestine including:

a—a protective device (5) comprising an anchor element consisting of a stent (1) and a flexible outer sheath (2), and b—an introducer (10) comprising at least a first deformable guide tube (12), characterized in that the downstream end of said outer sheath is connected to said first guide tube (12) or to a first connecting piece (11), said outer sheath (2) being folded inside said first deformable guide tube (12), said stent being held in radial compression inside said first deformable guide tube.

20 Claims, 12 Drawing Sheets

(51) Int. Cl.
  *A61B 17/115* (2006.01)
  *A61F 2/04* (2013.01)
(52) U.S. Cl.
  CPC . *A61B 2017/1132* (2013.01); *A61B 2217/005* (2013.01); *A61F 2002/045* (2013.01)

(56) References Cited

U.S. PATENT DOCUMENTS

| | | |
|---|---|---|
| 4,627,837 A | 12/1986 | Gonzalo |
| 4,716,900 A | 1/1988 | Ravo et al. |
| 4,721,109 A | 1/1988 | Healey |
| 5,425,739 A | 6/1995 | Jessen |
| 5,534,007 A | 7/1996 | St. Germain et al. |
| 5,558,642 A | 9/1996 | Schweich, Jr. et al. |
| 5,594,038 A | 1/1997 | Kobayashi et al. |
| 6,068,636 A | 5/2000 | Chen |
| 6,325,798 B1 | 12/2001 | Edwards et al. |
| 6,398,758 B1 | 6/2002 | Jacobsen et al. |
| 6,514,282 B1 | 2/2003 | Inoue |
| 6,585,926 B1 | 7/2003 | Mirzaee |
| 6,733,519 B2 | 5/2004 | Lashinski et al. |
| 6,808,492 B2 | 10/2004 | Snyder |
| 6,926,724 B1 | 8/2005 | Chu |
| 7,025,791 B2 | 4/2006 | Levine et al. |
| 7,147,627 B2 | 12/2006 | Kim et al. |
| 7,267,694 B2 | 9/2007 | Levine et al. |
| 7,267,794 B2 | 9/2007 | Amick |
| 7,316,716 B2 | 1/2008 | Egan |
| 7,347,875 B2 | 3/2008 | Levine et al. |
| 7,509,175 B2 | 3/2009 | Sparks et al. |
| 7,547,312 B2 | 6/2009 | Bauman et al. |
| 7,643,887 B2 | 1/2010 | Imran |
| 7,678,090 B2 | 3/2010 | Risk, Jr. et al. |
| 7,766,973 B2 | 8/2010 | Levine et al. |
| 7,776,081 B2 | 8/2010 | Zuidema et al. |
| 7,815,591 B2 | 10/2010 | Levine et al. |
| 8,083,758 B2 | 12/2011 | Hsu et al. |
| 8,114,045 B2 | 2/2012 | Surti |
| 8,118,774 B2 | 2/2012 | Dann et al. |
| 8,167,859 B2 | 5/2012 | Shah et al. |
| 8,182,527 B2 | 5/2012 | Llanos et al. |
| 8,187,254 B2 | 5/2012 | Hissink et al. |
| 8,211,186 B2 | 7/2012 | Belhe et al. |
| 8,282,598 B2 | 10/2012 | Belhe et al. |
| 8,323,229 B2 | 12/2012 | Shin et al. |
| 8,398,669 B2 | 3/2013 | Kim |
| 8,491,612 B2 | 7/2013 | Stopek et al. |
| 8,597,224 B2 | 12/2013 | Vargas |
| 8,636,810 B2 | 1/2014 | Rousseau |
| 8,690,817 B2 | 4/2014 | Assaf et al. |
| 8,702,641 B2 | 4/2014 | Belhe et al. |
| 8,702,642 B2 | 4/2014 | Belhe et al. |
| 8,753,407 B2 | 6/2014 | Nguyen |
| 8,801,647 B2 | 8/2014 | Melanson et al. |
| 8,821,429 B2 | 9/2014 | Vargas |
| 8,828,090 B2 | 9/2014 | Terliuc |
| 8,900,268 B2 | 12/2014 | Weidenhagen et al. |
| 8,926,593 B2 | 1/2015 | Croizat et al. |
| 9,044,300 B2 | 6/2015 | Belhe et al. |
| 9,173,734 B2 | 11/2015 | Vargas |
| 9,265,640 B2 | 2/2016 | Harris et al. |
| 9,339,272 B2 | 5/2016 | Khosrovaninejad |
| 9,398,982 B2 | 7/2016 | Kleiner |
| 9,402,630 B2 | 8/2016 | Stopek et al. |
| 9,511,208 B2 | 12/2016 | Assaf et al. |
| 9,675,360 B2 | 6/2017 | Baker |
| 9,687,334 B2 | 6/2017 | Williams et al. |
| 9,750,596 B2 | 9/2017 | Levine et al. |
| 9,789,291 B2 | 10/2017 | Assaf et al. |
| 9,827,135 B2 | 11/2017 | Fong et al. |
| 9,980,727 B2 | 5/2018 | Khosrovaninejad |
| 10,456,138 B2 | 10/2019 | Khosrovaninejad |
| 10,835,248 B2 | 11/2020 | Khosrovaninejad |
| 2004/0044358 A1 | 3/2004 | Khosravi et al. |
| 2004/0107004 A1 | 6/2004 | Levine et al. |
| 2004/0122527 A1 | 6/2004 | Imran |
| 2005/0004663 A1 | 1/2005 | Llanos et al. |
| 2005/0228409 A1 | 10/2005 | Coppi |
| 2005/0255230 A1 | 11/2005 | Clerc et al. |
| 2005/0256587 A1 | 11/2005 | Egan |
| 2006/0064120 A1 | 3/2006 | Levine et al. |
| 2006/0112536 A1 | 6/2006 | Herweck et al. |
| 2007/0032879 A1 | 2/2007 | Levine et al. |
| 2007/0045229 A1 | 3/2007 | Keenan et al. |
| 2007/0262161 A1 | 11/2007 | Davies |
| 2007/0282452 A1 | 12/2007 | Weitzner et al. |
| 2008/0033244 A1 | 2/2008 | Matsui et al. |
| 2008/0039878 A1 | 2/2008 | Williams et al. |
| 2008/0161717 A1 | 7/2008 | Gertner |
| 2008/0167606 A1 | 7/2008 | Dann et al. |
| 2008/0195226 A1 | 8/2008 | Williams et al. |
| 2008/0208325 A1 | 8/2008 | Helmus et al. |
| 2008/0208357 A1 | 8/2008 | Melanson et al. |
| 2008/0255592 A1 | 10/2008 | Hsu et al. |
| 2009/0018606 A1 | 1/2009 | Sparks et al. |
| 2009/0220677 A1 | 9/2009 | Clerc et al. |
| 2009/0276055 A1 | 11/2009 | Harris et al. |
| 2010/0010519 A1 | 1/2010 | Stopek et al. |
| 2011/0202084 A1 | 8/2011 | Hoem et al. |
| 2011/0295288 A1 | 12/2011 | Khosrovaninejad |
| 2012/0095541 A1 | 4/2012 | Kramann |
| 2013/0006382 A1 | 1/2013 | Behan |
| 2013/0087597 A1 | 4/2013 | Shelton, IV et al. |
| 2013/0274717 A1 | 10/2013 | Dunn |
| 2013/0304101 A1 | 11/2013 | Stopek et al. |
| 2014/0088622 A1 | 3/2014 | Rousseau |
| 2014/0118029 A1 | 5/2014 | Tseng et al. |
| 2014/0163664 A1 | 6/2014 | Goldsmith |
| 2014/0222039 A1 | 8/2014 | Khosrovaninejad |
| 2014/0350694 A1 | 11/2014 | Behan |
| 2014/0371870 A1 | 12/2014 | Terliuc |
| 2015/0045715 A1 | 2/2015 | Assaf et al. |
| 2016/0220256 A1 | 8/2016 | Khosrovaninejad |
| 2017/0027729 A1 | 2/2017 | Abu Dayyeh |
| 2017/0071780 A1 | 3/2017 | Fong et al. |
| 2017/0087343 A1 | 3/2017 | Assaf et al. |
| 2017/0189217 A1 | 7/2017 | Folan et al. |
| 2017/0265849 A1 | 9/2017 | Assaf et al. |
| 2018/0235631 A1 | 8/2018 | Khosrovaninejad |
| 2021/0008336 A1 | 1/2021 | Rajagopalan et al. |
| 2021/0038224 A1 | 2/2021 | Khosrovaninejad |
| 2021/0315578 A1 | 10/2021 | Khosrovaninejad |

FOREIGN PATENT DOCUMENTS

| | | |
|---|---|---|
| CN | 103764069 A | 4/2014 |
| CN | 204169953 U | 2/2015 |
| CN | 108261577 A | 7/2018 |
| EP | 1405612 A1 | 4/2004 |
| EP | 2143389 A1 | 1/2010 |
| EP | 2165665 A1 | 3/2010 |
| EP | 2143388 B1 | 6/2011 |
| EP | 1556097 B1 | 8/2011 |
| EP | 1746941 B1 | 11/2011 |
| EP | 2395942 A1 | 12/2011 |
| EP | 2347723 B1 | 12/2012 |
| EP | 2286739 B1 | 1/2013 |
| EP | 2604195 A1 | 6/2013 |
| EP | 1492585 B1 | 6/2016 |
| EP | 2143387 B1 | 12/2016 |
| EP | 1647231 B1 | 11/2017 |
| FR | 2846868 A1 | 5/2004 |
| FR | 2941858 A1 | 8/2010 |
| JP | 2000316979 A | 11/2000 |
| JP | 2005519709 A | 7/2005 |
| JP | 2005524485 A | 8/2005 |
| JP | 2007069003 A | 3/2007 |
| JP | 2007513685 A | 5/2007 |
| JP | 2010502289 A | 1/2010 |
| JP | 2012517255 A | 8/2012 |
| JP | 2014527854 A | 10/2014 |
| WO | WO-03094785 A1 | 11/2003 |
| WO | WO-2007045229 A1 | 4/2007 |
| WO | WO-2008030403 A1 | 3/2008 |

(56) References Cited

FOREIGN PATENT DOCUMENTS

| WO | WO-2010002291 A1 | 1/2010 |
|---|---|---|
| WO | WO-2010009291 A1 | 1/2010 |
| WO | WO-2010092291 A1 | 8/2010 |
| WO | WO-2011085234 A1 | 7/2011 |
| WO | WO-2011120047 A1 | 9/2011 |
| WO | WO-2013014353 A1 | 1/2013 |
| WO | WO-2013014355 A1 | 1/2013 |
| WO | WO-2013026474 A1 | 2/2013 |
| WO | WO-2014193949 A2 | 12/2014 |
| WO | WO-2017191500 A1 | 11/2017 |
| WO | WO-2017201504 A1 | 11/2017 |
| WO | WO-2018089773 A1 | 5/2018 |
| WO | WO-2019077218 A1 | 4/2019 |
| WO | WO-2020152640 A1 | 7/2020 |

OTHER PUBLICATIONS

Extended European Search Report for European Application No. 22170158.4, dated Oct. 11, 2022, 8 pages.
International Search Report and Written Opinion dated Aug. 19, 2022 in Int'l PCT Patent Application Serial No. PCT/US2022/026558, 10 pages
International Search Report and Written Opinion dated Mar. 20, 2019 in Int'l PCT Appl. Serial No. PCT/FR2018/052388, 06 pages.
International Search Report and Written Opinion dated May 7, 2010 in Int'l PCT Patent Application Serial No. PCT/FR2010/050210, 6 pages.
International Search Report and Written Opinion dated Sep. 4, 2012 in Int'l PCT Patent Appl. Serial No. PCT/FR2012/051576, 7 pages.
International Search Report and Written Opinion from corresponding PCT Application No. PCT/FR2020/050889, dated Sep. 10, 2020, 6 pages.
Moon CM., et al., "Comparison of a Newly Designed Double-Layered Combination Covered Stent and D-Weave Uncovered Stent for Decompression of Obstructive Colorectal Cancer: A Prospective Multicenter Study", Dis Colon Rectum, 2010, vol. 53, pp. 1190-1196.
Shim CS., et al., "Through-the-Scope Double Colonic Stenting in the Management of Inoperable Proximal Malignant Colonic Obstruction: a Pilot Study", Endospcopy, 36(05):426-431 (May 2004).
Shomura Y., et al., "Composite Material Stent Comprising Metallic Wire and Polylactic Acid Fibers, and Its Mechanical Strength and Retrievability", Acta Radiol., May 2009, vol. 50, No. 4, pp. 355-359.
U.S. Appl. No. 13/147,199 / U.S. Pat. No. 9,339,272, filed Aug. 11, 2011 May 17, 2016.
U.S. Appl. No. 14/234,834 / U.S. Pat. No. 9,980,727, filed Jan. 24, 2014 May 29, 2018.
U.S. Appl. No. 15/097,491 / U.S. Pat. No. 10,456,138, filed Apr. 13, 2016 Oct. 29, 2019.
U.S. Appl. No. 15/959,553 / U.S. Pat. No. 10,835,248, filed Apr. 23, 2018 Nov. 17, 2020.
U.S. Appl. No. 16/647,152 / U.S. Pat. No. 11,589,869, filed Mar. 13, 2020 Feb. 28, 2023.
U.S. Appl. No. 17/071,034, filed Oct. 15, 2020.
U.S. Appl. No. 17/618,715, filed Dec. 13, 2021.
U.S. Appl. No. 17/730,125, filed Apr. 26, 2022.

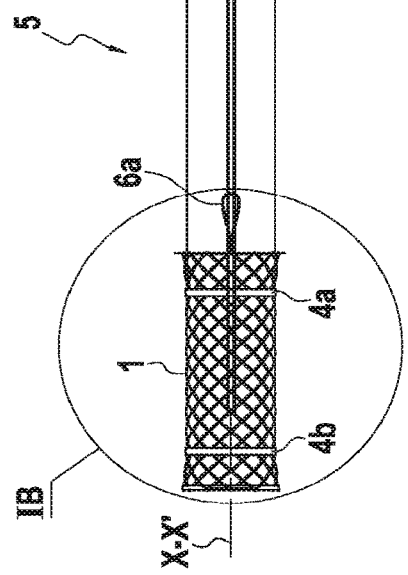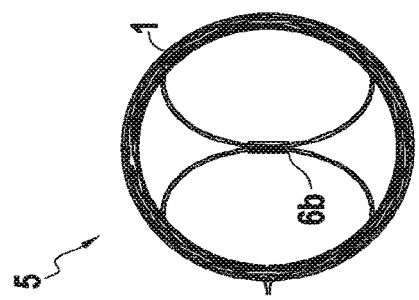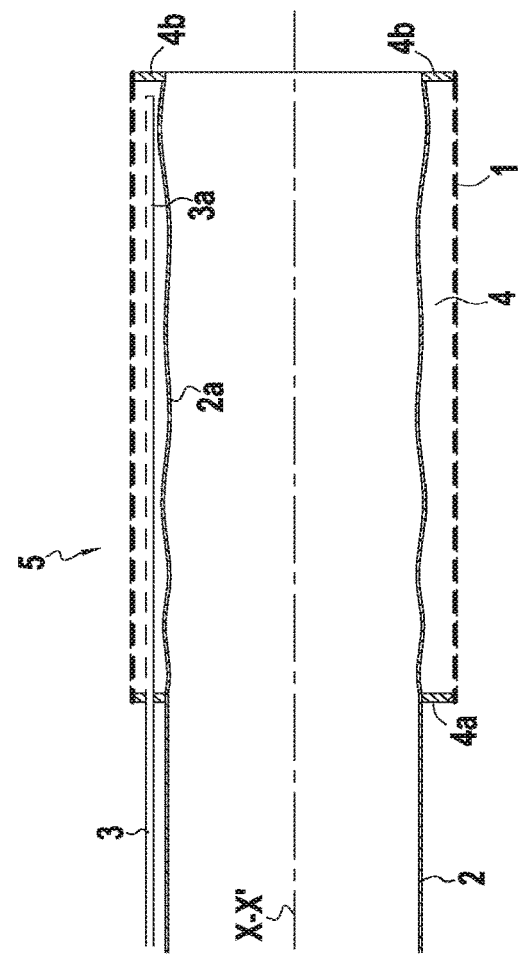

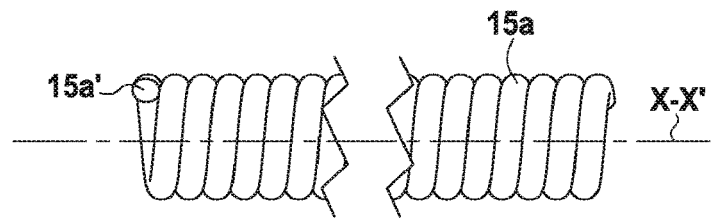 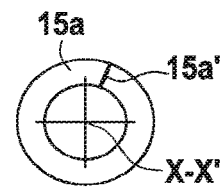
FIG.3A    FIG.3B
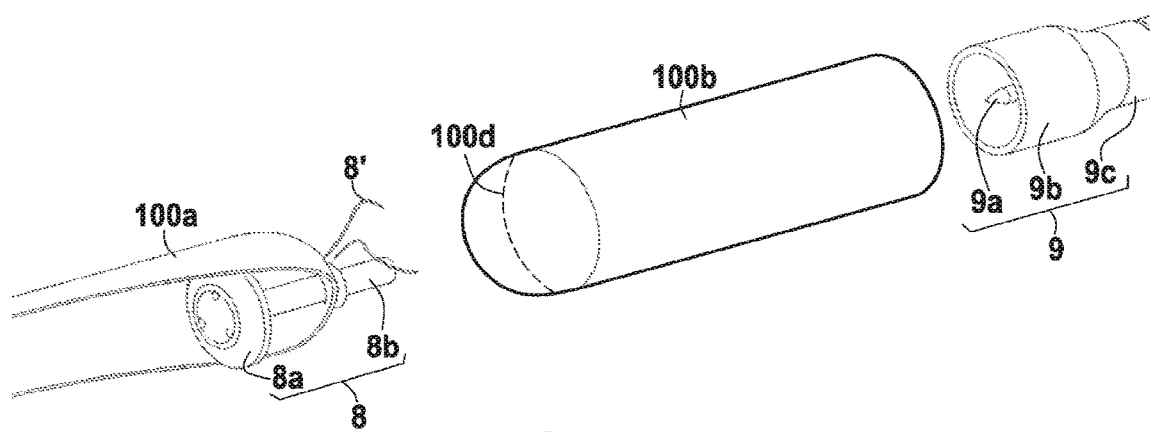
FIG.4A
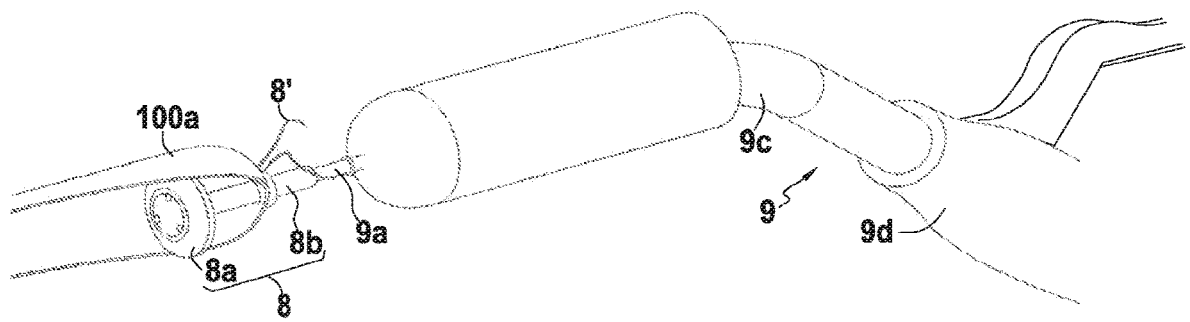
FIG.4B

COMPLEX SURGICAL DEVICE FOR CARRYING OUT AND PROTECTING AN ANASTOMOSIS

CROSS-REFERENCE TO RELATED APPLICATIONS

This application is a continuation of U.S. patent application Ser. No. 16/647,152, filed Mar. 13, 2020, now U.S. Pat. No. 11,589,869, which is a U.S. national stage application of PCT/FR2018/052388, filed Sep. 28, 2018, which claims priority to French Patent Application Serial No. 1759847, filed Oct. 19, 2017, the entire contents of each of which are incorporated herein by reference.

The present invention relates to a complex surgical device useful for carrying out and protecting an intestinal anastomosis.

Colorectal anastomoses have a disunion rate of about 20%. Disunion of an anastomosis (fistula) is a serious complication with a mortality rate of about 20%. To reduce the deleterious consequences of anastomotic fistulas, some patients benefit from an outlet (a stoma) between the skin and the intestine located upstream of the anastomosis to divert the digestive flow into an external pouch and avoid contact between the anastomosis and the feces. The stoma is closed in a second step after the anastomosis has healed. The presence of a stoma and the need for re-intervention to remove it is a significant burden on the patient and a significant source of health expenditure.

It is in this context that an anastomosis protection device described in FR 2 941 858 and EP 2 395 942 has been provided which allows fecal matter to be diverted into the intestinal lumen and ostomies avoided. The device consists of a flexible outer sheath attached to a stent downstream of the stent, the stent being intended to be anchored upstream of the anastomosis. The stent is the temporary anchor element to the walls of the intestine, which holds the sheath in place and the sheath serves to divert fecal matter towards the anal orifice without contact with the intestinal wall at the anastomosis and thus protect the anastomosis.

In WO 2013/014353, this device was further developed by adding means to control the anchoring or release of the stent from the intestinal wall. To do this, the device's anchorage or release is reinforced by means of a tube opening into the space of a chamber delimited between an inner sheath and the stent wall, which makes it possible to create a suction effect by drawing the walls of the intestine against the stent to reinforce the anchorage or, on the contrary, to insufflate air or a fluid to release it.

To do this, the surgical device of WO2013/014353 essentially consists of taking advantage of the viscoelasticity of the intestine to attract its inner wall towards the outer wall of the stent. Indeed, the intestinal mucosa is flexible and elastic while the stent walls are relatively rigid. The intestinal wall can be attracted (by suction) and bonded to the outer walls of the stent under the effect of negative pressure in the stent-mucosa interface. In this case, the frictional force between the intestine and the stent increases rapidly and significantly due to a kind of suction effect. As a result, the mobility of the stent becomes closely related to the suction effect, the modulation of which then influences the behavior of the stent in the intestine.

More precisely in this patent WO 2013/014353 a surgical anchoring device is described, capable of anchoring itself to the mucous membrane of the internal wall of the intestine comprising:

(a) a temporary anchor element whose anchoring can be modified in a controlled manner, comprising at least a first semi-rigid hollow longitudinal element of the stent type, defining a wall of revolution about a longitudinal axis comprising a substantially cylindrical multi-perforated current part with a substantially circular cross-section called the first wall, said first hollow longitudinal element being made of a material giving it radial elasticity properties so that it can be radially compressed in a retracted position and adopt a said position of maximum radial expansion after release of the radial compression such that said first multi-perforated wall has a first external diameter which can be varied in a controlled manner between:

a first minimum external diameter in said retracted radial position of said first wall of not more than 20 mm, preferably not more than 10 mm, and a first maximum external diameter at said maximum radial expansion position of said first wall, preferably 18 to 45 mm, and (b) a flexible outer sheath attached to said stent and extending from its downstream end, characterized in that at least part, preferably the entire length, of the cylindrical inner surface of said first wall is lined with an independent sealing layer forming an inner sheath, only the longitudinal ends of said inner sheath being attached in a sealed manner to said anchor element by means of first sealing means, preferably by joint fusing or an annular seal of elastomeric glue, at each said longitudinal end of said inner sheath, so as to delimit a chamber referred to as a vacuum chamber between said inner sheath and said first wall, said temporary anchor element being coupled to a flexible or semi-rigid tube referred to as an injection-suction tube, extending outside said anchor element, an open end of said injection-suction tube opening into said vacuum chamber.

More particularly, said injection-suction tube is connected, preferably reversibly at its free longitudinal end, to a connecting endpiece, itself reversibly connected or capable of being reversibly connected with a device for injecting or sucking up air or liquid such as a syringe, said connecting endpiece comprising a shut-off device, preferably an anti-backflow valve, and a vacuum indicator device capable of indicating the content of the vacuum in said vacuum chamber, in particular located on a vacuum ampoule.

Said chamber defines a sealed chamber between the sealed film of the inner sheath and the intestinal wall when said anchor element is in a position of maximum expansion and immobilized by anchoring against the inner surface of the intestinal wall. And, in the event of detachment of said anchor element and/or in the event of migration of said anchor element inside the intestine, said chamber loses its seal. However, air can then be sucked through said tube from its free end from the outside of the patient in order to draw the intestinal wall against the external surface of said first wall over a part or even over the entire external surface of said first wall delimiting said chamber in order to stop the migration of the anchor element by restoring the vacuum in said chamber and thus the sealing of said chamber.

Said anchor element may be held in a radially retracted position with an instrument called an "introducer" described below, the radial expansion taking place after the anchor element has been released from the introducer.

In WO 2013/014353, the introducer can be in a known manner constituted by a semi-rigid guide tube, of the catheter type provided at one of its ends with a handle and whose internal diameter and length make it possible to keep housed therein said anchor element in its retracted form and said sheath, preferably longitudinally extended.

In WO 2013/014353, for anal introduction, said device further comprises an introducer instrument comprising:

a tubular outer sheath capable of containing and holding said anchor element compressed in said retracted position and said injection-suction tube within the distal end of said outer sheath, and long enough to further contain said sheath and said injection-suction tube, said outer sheath preferably being at least 70 cm long, preferably at least 100 cm, and means for routing the distal end of said introducer from the anal orifice to said anchoring site in the intestine upstream of the anastomosis, and preferably means for disengaging said anchor element from the outer casing, preferably still consisting of a stop tube having a stop at its distal end, in contact if necessary with the longitudinal end of said anchor element, said sheath downstream of the anchor element surrounding said stop tube inside said outer casing.

An anastomosis is performed in the known manner with a stapler by inserting a circular cross-section part called an "anvil" into the intestine upstream of the anastomosis site, at the level of the free end of the intestine then tightening a wire known as "purse string" around the anvil shaft before engaging the stapler body in the downstream part of the anastomosis up to the level of the anvil shaft to make the circular stapler cooperate with the anvil for the sectioning of the tissues and the placing of the staples.

In these earlier patents cited above, the anastomosis protection device is therefore placed in the intestine once the anastomosis has been carried out with a stapler, for example of the type described in FR 2 846 868. It is by means of a flexible introducer that the device is introduced through the anal orifice and then the anastomosis and then the intestine located upstream of the anastomosis. After removal of the introducer, the stent opens in radial extension and comes into contact with the walls of the intestine while the sheath and suction tube deploy in the lumen of the intestine from its anchoring site upstream of the anastomosis to the anal orifice through the anastomosis.

Despite the proven safety of these maneuvers, some surgeons remain reluctant to introduce an object through a fresh anastomosis as described in WO 2013/014355.

According to the present invention, a protective device is provided which can be introduced into the intestine even before the anastomosis is made, this also in order to facilitate the anastomosis with the anvil and stapler, to reduce the number of steps during the surgical procedure and to reduce the operating time.

To this end, in principle, the object of the present invention is:

means for placing the anastomosis protection device in the intestinal lumen upstream of an anastomosis not requiring instruments introduced through the anal orifice and through the freshly performed anastomosis but using excision of pathological intestine and opening of the upstream intestinal lumen required for the stapler anvil for prior placement of the anastomosis protection device, and means for deploying the anchoring device, the outer sheath and, if applicable, the suction tube through the anastomosis only after the anastomosis has been performed, the deployment of the sheath and the suction tube taking place by and with the removal of the stapler, i.e. after the steps of:

closing the upper intestine on the axis of the anvil by means of a purse string, introducing the stapler body through the anal orifice into the downstream intestine, and securing the anvil to the stapler body, stapling, and removing the anvil and stapler through the anal orifice.

For this purpose, the present invention more precisely provides a complex surgical device consisting of a ready-to-use assembly for performing an anastomosis in the intestine with an anvil and a circular stapler and then protecting said anastomosis in the intestine comprising:

(a) a protective device comprising an anchor element consisting of at least one stent capable of being temporarily anchored to the inner wall of the intestine upstream of the anastomosis and a flexible outer sheath, at least the upstream end of which is fixed to said stent, said outer sheath being capable of extending downstream of said anchor element and downstream of said anastomosis in order to allow said anastomosis to be protected, in particular after said anastomosis has been performed and said anvil and stapler have been removed, and (b) at least a first tube, called first guide tube, said stent being held in radial compression within said first tube, preferably at a distal end of said first guide tube, said first tube being part of a guide tube of an introducer device or being adapted to be reversibly attached to an introducer device, said first tube being deformable in curvature relative to its longitudinal axis (XX'), characterized in that said flexible sheath is stored, preferably folded, inside said first guide tube, and possibly partly, or even entirely, inside said stent, the downstream end of said sheath being connected to said first guide tube or to a first connection piece independent of said first guide tube, said flexible sheath being able to be deployed downstream of said stent by withdrawing the proximal end of said first guide tube or respectively to said first connection piece to which it is fixed.

More particularly, the proximal end of said first guide tube or respectively said first connecting piece comprises reversible fixing means such that said proximal end is capable of being fixed in a reversible manner to a said anvil, said flexible sheath being capable of being deployed downstream of said stent by the withdrawal of said anvil fixed in a reversible manner to the proximal end of said first guide tube or respectively to said first connecting piece.

More particularly, the proximal end of said first guide tube or respectively said first connecting piece comprise means for reversible attachment to the front face of a said anvil by gluing, screwing, clamping or magnetic connection. It is understood that the removal of said anvil implies the prior disassociation of said anvil with respect to said proximal end of said first guide tube or respectively of said first connecting part.

In a known manner, a said introducer comprises at least (i) said first deformable guide tube, (ii) a second rigid guide tube, the proximal end of said first deformable guide tube being attached or attachable to the distal end of said second rigid guide tube, (iii) a handle connected to the proximal end of said second rigid guide tube, and (iv) a pusher extending from said handle within said second rigid guide tube and said first deformable guide tube comprising a pusher rod and a pusher stop at the distal end of the pusher rod.

In a known manner, said introducer is capable of allowing the implantation of the protective device upstream of the anastomosis site, said pusher stop being capable of pushing said protective device outside the distal end of said first deformable guide tube to allow the radial extension and anchoring of said stent against the wall of the intestine, the proximal end of said pusher rod being capable of cooperating with said handle by manually controlling a relative translation of said pusher rod with respect to the first deformable guide tube.

In the prior art, this type of introducer is used to introduce the stent only after the anastomosis has been performed and said first deformable guide tube is longer than according to the invention because it must extend from the anal orifice to upstream of the anastomosis, i.e. in practice at least 45 cm.

According to the present invention, the introducer is used to introduce the stent before the anastomosis is carried out so that the length of said first deformable guide tube is for example no more than 30 cm, in order to place the stent upstream of the anastomosis site.

Thus the removal of the introducer after anchoring of said protective device upstream of the anastomosis makes it possible to partially deploy said sheath in the intestine downstream of the anastomosis, the complete deployment of said external sheath taking place during the removal of the stapler, via the anal orifice. Indeed, after the removal of the parts of the introducer other than said first connecting piece or said first tube of the introducer attached to said outer sheath, the latter may be reversibly attached directly or indirectly to a stapler anvil in order to perform the anastomosis as explained below.

More particularly still, when the downstream end of said sheath is attached to a said first connecting piece, said first connecting piece is positioned just downstream of said stent, and said means for reversible attachment of said first connecting piece, may serve successively to:
- −1) attaching to an abutment of a pusher of said introducer during the initial phase of introduction to release said stent out upstream of said first guide tube at the end of the initial phase of introduction under the effect of the thrust of said pusher, said stent thus being found in the upstream intestine at a certain distance preferably 10 to 20 cm upstream of the anastomosis site, then
- −2) to be fixed to a said anvil after detachment and withdrawal of said pusher and of the assembly of said introducer, to allow said anastomosis to be performed with a stapler, optionally after partial deployment of said sheath downstream of the stent by withdrawal of said pusher up to the level of the site of the anastomosis before detachment of said pusher, the complete deployment of said sheath downstream of said anastomosis resulting from the withdrawal of the assembly integral with said first connecting parts, said anvil and said stapler after said anastomosis has been performed.

More particularly still, when the downstream end of said sheath is connected to said first tube, said first tube is capable of being reversibly attached to an introducer device, said reversible attachment means at the proximal end of said first guide tube serving successively to:
- −1) be fixed to the end of a second guide tube of the introducer, which is integral with the handle and the pusher, during the initial phase of introduction, then
- −2) to be fixed to said anvil, after detachment of said first guide tube and removal of the remainder of said introducer including removal of said pusher, to allow said anastomosis to be performed with an anvil and a stapler, optionally after partial deployment of said sheath downstream of the stent by moving back from said first tube to the site of the anastomosis, the complete deployment of said sheath downstream of said anastomosis resulting from the complete removal of the assembly integral with said first guide tube, said integral anvil and said stapler, after said anastomosis has been performed.

The invention is more particularly advantageous when the protective device comprises at least one flexible tube called a suction tube, preferably two suction tubes, each suction tube being capable of extending outside said stent downstream thereof, in particular after carrying out said anastomosis and removing said anvil and stapler, an open end of said suction tube opening into the interior of the stent in a vacuum chamber delimited between the inner wall of the stent and an inner film covering the inner wall of the stent, preferably said film constituting an extension of said sheath, characterized in that each said suction tube is stowed, preferably folded, preferably further helically wound inside said first guide tube, and optionally partly or even entirely inside said stent, the downstream end of each said suction tube being connected to said first guide tube or to a said first connecting piece, each said suction tube being capable of being deployed downstream of said stent by the removal of said anvil reversibly attached to the proximal end of said first guide tube or respectively to said first connecting piece.

The open end of the suction tube preferably consists of a terminal part of the tube within said chamber perforated by multiple perforations.

The use of two suction tubes increases the anchoring force and protects against failure of the first suction tube, for example if the first suction tube becomes blocked.

More particularly, a complex ready-to-use device according to the invention can be implemented in a surgical treatment process with the aid of a complex surgical device according to the invention in which the following successive steps are carried out in which:
- S1) said surgical device is introduced into the intestine by the abdominal route in the part of the intestine upstream of the anastomosis site with an introducer device comprising or attached to a first guide tube and said anchor element is released upstream of the anastomosis site by actuating a pusher inside said first guide tube,
- S2) the parts of said introducer other than said first guide tube or other than a said first connecting piece to which or respectively to which said sheath and said suction tube are attached are removed from the intestine,
- S3) a stapler anvil is inserted which is reversibly fixed to the proximal end of said first guide tube or to said first connecting piece,
- S4) the sectioning of the intestinal tissue of the anastomosis area and the preparation of the anastomosis is carried out by stapling with a stapler cooperating with the anvil,
- S5) the stapler attached to the anvil, itself attached to said first tube or to said first connecting piece is removed, which causes said sheath and said suction tube to deploy, and
- S6) after passing through the anal orifice, the downstream ends of said outer sheath and said suction tube are disengaged, preferably with scissors, from said first guide tube or said first connecting piece, outside said anal orifice, and
- S7) the downstream end of the suction tube is connected to a device outside the patient capable of maintaining the vacuum in the vacuum chamber and thus preventing migration of said anchor element.

This procedure is particularly useful for the temporary protection of an anastomosis on the large intestine or colon, rectum or anal canal, to prevent or reduce the risk of anastomotic fistula. In this case, preferably, the distance between said anchoring position upstream of said anastomosis and said anastomosis is at least equal to 10 cm. More particularly, the distance between the anastomosis and the anchoring site is at most 20 cm.

As explained below, the device according to the invention, because of its possible implantation before the anastomosis is performed, makes it possible to implement a stent and a sheath of reduced dimensions on the one hand and therefore implanted at a reduced distance upstream of the site of the anastomosis compared to what was required in previous designs such as in WO 2013/014355, in particular at a distance of only 10 to 20 cm.

The term "anastomosis protection", as used here, means protection of the anastomosis when the intestinal transit is resumed.

"Downstream" and "upstream" refer here to the direction of travel from upstream to downstream of intestinal transit and to a position when the devices concerned are in place in the intestine to fulfil their function. By "downstream end" of said sheath, it is understood that it is the end intended to be deployed in said stent once deployed after removal of the stapler after completion of the anastomosis, even if this downstream end is initially brought closer to the upstream end in order to be fixed to the inner wall of the first guide tube.

The terms "proximal" and "distal" refer here to the position in or of the element concerned in relation to the site of initial introduction into the patient's body and in practice here also in relation to the handle of the introducer with regard to the elements of the introducer. The proximal and upstream ends correspond to the downstream and upstream ends respectively for introduction through the anal orifice or a part of the intestine downstream of the anastomosis.

In this case according to the invention, only the first deformable guide tube of the introducer and part of said second rigid guide tube are introduced into the lumen of the part of the intestine upstream of the anastomosis, the rest of the second rigid guide tube and the handle remaining outside the intestine.

The term "first deformable guide tube" of the introducer means in practice a semi-flexible tube made of elastomer or PU material thicker than said sheath and deformable by bending in relation to its longitudinal axis until it can adopt a 90° external curvature. This first deformable guide tube has graduations enabling the implantation site to be checked before release.

More particularly, in a known manner, said sheath is fixed in a sealed manner to said anchor element by means of sealed fixing means, preferably by fusing joint or an annular joint of elastomer glue, at each said longitudinal end of said inner sheath, so as to delimit a vacuum chamber between said inner sheath and said first wall, said temporary anchor element being coupled to said flexible or semi-rigid tube called suction tube, extending outside said anchor element, an open end of said suction tube opening into said vacuum chamber.

In a first embodiment, the downstream end of said sheath and the downstream end of said suction tube(s) are connected to the distal end of said first guide tube, the proximal end (or downstream end) of said first guide tube comprising a second connecting piece fixed or capable of being fixed in a reversible manner to the distal end (or upstream end) of a second rigid guide tube of an introducer device for the introduction of the protective device upstream of the site of the anastomosis and then capable of being fixed in a reversible manner to a said anvil for carrying out the anastomosis.

The second connecting piece is fixed or capable of reversibly fixing said first guide tube to the distal end of a second rigid guide tube of an introducer device in order to connect them for the introduction of the protective device upstream of the anastomosis site and then to disconnect them for the removal of the introducer before the anvil and stapler are used.

In this first embodiment, said first guide tube comprising a second connecting piece at its proximal end remains inserted in the intestine during the making of the anastomosis and is withdrawn from the intestine when the stapler is removed after the making of the anastomosis because of its connection with the anvil thus allowing the complete unfolding and deployment of said sheath and said suction tube downstream of said stent because of their connection with said first tube.

More particularly, in this first embodiment, the downstream end of said sheath and the downstream end of said suction tube(s) are connected to the distal end (or upstream end) of said first guide tube by adhesive bonding or by a thread.

In this first embodiment, more particularly, the sheath and the suction tube(s) are entirely arranged, in particular folded or rolled, inside the stent except for their downstream parts which leave the stent at its downstream end to join the upstream end of the first guide tube upstream of the stent, these external parts of the sheath and the suction tube(s) being interposed between the stent and the internal wall of the first guide tube.

More particularly, in this first embodiment, said second connecting piece is fixed or capable of being fixed in a reversible manner to an adapter which is itself capable of being fixed in a reversible manner to a stapler anvil.

More particularly still, in this first embodiment, said second connecting part is fixed or capable of being fixed in a reversible manner by screwing, gluing, clamping or magnetic connection, to an adapter which is itself capable of being fixed in a reversible manner to a said stapler anvil, by gluing, clamping or magnetic connection.

More particularly still, in this first embodiment, said second connecting piece comprises a threaded element capable of cooperating by screwing with:
  a first complementary threaded element located at the distal end of said second rigid guide tube, and then
  a second complementary threaded element located at the distal end of a said adapter.

It is understood that:
  said second connecting piece is reversibly attached to the distal end of said second rigid guide tube, during the introduction and release of the protective device by said pusher to allow the introduction and then anchoring of said stent in the intestine upstream of the site of said anastomosis before the anastomosis is performed, and
  said second connecting piece is reversibly attached to said anvil or a said adapter after removal of said pusher for reversible attachment of the anvil to allow said anastomosis to be performed with said stapler after said stent has been anchored in the intestine upstream of the site of said anastomosis.

More particularly, the flat proximal part of a said adapter is suitable for attachment by adhesive bonding to the flat front face of a said anvil.

In a second embodiment, the downstream end of said sheath and preferably the downstream end of said suction tube(s) is (or are) connected to a said first connecting piece, at least one proximal end of which is disposed outside the downstream end of said stent.

More particularly, in this second embodiment, the downstream end of said sheath and preferably the downstream end of said suction tube(s) is (or are) connected to a distal part of said first connecting piece independent of said first guide tube, preferably a tubular distal portion arranged or adapted to be arranged inside the downstream end of said stent, and a proximal portion of said first connecting piece is arranged outside and at the downstream end of said stent preferably having a flat proximal face of larger diameter than said tubular distal portion.

Thus, initially and during the introduction phase, said first connecting piece is arranged inside said first guide tube.

In this second embodiment, more particularly, the sheath and the suction tube are entirely stored inside the stent except for their swallowed parts which come out of the stent at its swallowed end to join the first connecting piece which is placed against the swallowed end of the stent.

In this second embodiment, the entire protective device and said first connecting piece are independent of the first guide tube and the introducer.

More particularly, the downstream end of said sheath and the downstream end of said suction tube(s) are connected to a said first connecting piece by adhesive bonding or by a wire.

More particularly still, in this second embodiment, said first connecting part is adapted to be fixed in a reversible manner to a stop of a pusher rod inside said first guide tube when the protective device is introduced upstream of the anastomosis site, preferably by gluing, screwing, clamping or magnetic connection.

More particularly still, in this second embodiment, said first connecting part is suitable for reversible direct attachment to a said anvil by gluing, screwing, clamping or magnetic connection, preferably by adhesive bonding.

In this embodiment, the introducer device can be completely removed from the intestine after introduction of the protective device upstream of the anastomosis site before the anastomosis is carried out, only said first connecting piece remaining introduced into the intestine to be fixed to the anvil for the purpose of carrying out the anastomosis, said first connecting piece being withdrawn from the intestine when the stapler is removed after the anastomosis has been performed because of its connection with the anvil, thus allowing the complete deployment of said sheath and of said suction tube(s) downstream of said stent because of their connection with said first connecting piece.

It is understood that:
said first connecting piece is reversibly attached to said pusher stop during the introduction and release of the protective device by said pusher to allow the introduction and anchoring of said stent in the intestine upstream of the site of said anastomosis before the anastomosis is performed, and
said first connecting piece is reversibly attached to said stapler anvil or to a said adapter after complete removal of said introducer to allow said anastomosis to be performed with said stapler after said stent has been anchored in the intestine upstream of the site of said anastomosis.

More particularly still, for both embodiments, the distal end of said first guide tube is closed by a flexible retaining element capable of retaining said protection device inside said first guide tube in the absence of thrust by a pusher rod stop, said retaining element being capable of deforming elastically and allowing the exit of said protection device under the effect of the thrust by said pusher rod stop.

More particularly still, the complex surgical device according to the invention comprises a said protective device and an introducer capable of allowing the implantation of the protective device upstream of the anastomosis site, said introducer comprising a handle fixed and/or capable of cooperating with the two following parts of the introducer:
(b1) a first deformable guide tube within which said stent is held in radial compression near the distal end of said first deformable guide tube, the proximal end of said first deformable guide tube being fixed to a second rigid guide tube integral with said handle, and
(b2) a pusher comprising a pusher rod deformable in curvature with respect to its longitudinal axis and a said pusher stop at the distal end of the pusher rod extending from the handle within said second rigid guide tube and said first deformable guide tube, the proximal end of said pusher rod being adapted to cooperate with said handle by manually controlling a relative translation of said pusher rod with respect to the first deformable guide tube.

More particularly, the pusher rod is a spiral rod formed by a steel wire wound helically along a virtual longitudinal axis XX' with coaxial contiguous turns of the same diameter, the diameter of the contiguous turns forming a deformable rod capable of being deformed in curvature with respect to said longitudinal axis to allow it to adopt a curvature to form a 90° bend.

More particularly still, said stent comprises at least one withdrawal loop at one end of its longitudinal ends, preferably two loops at each of its longitudinal ends.

The advantageous and novel features of the process for anchoring the stent and carrying out the anastomosis resulting from the novel structural features of the complex surgical device according to the invention are:
an anchoring of the protective device upstream of the anastomosis site, with deployment of said sheath and said suction tube and removal of the stapler in a single gesture after an anastomosis has been performed by a surgical stapler,
no passage of the introducer through the fresh anastomosis, and
reduction in operating time.

More particularly, the suction tube is a semi-rigid tube, in particular made of PE or PP, and has a length capable of holding in shape and extending inside the intestine from an anal orifice of the patient to said anchor element, preferably the length of said injection-suction tube being at least 20 cm, more particularly from 50 to 150 cm, and the free end of said suction tube outside the patient is connected to a device for sucking or injecting gaseous or liquid fluid, in particular air or a cold liquid as explained below.

More particularly, the length of the outer sheath protects the anastomosis and protrudes from the anal orifice when said anchor element is in the anchoring position and deployed downstream thereof.

Said outer sheath, due to its elastomeric constitution, has radial and longitudinal stretchability properties similar to those of the intestinal wall, which properties are those of an elastomeric material in the form of said sheath, the latter having radial and longitudinal elasticity properties. These radial and longitudinal elasticity properties of the sheath are similar to those of the wall of the colon.

In a preferred embodiment, said runner portion of said first wall extends from the upstream longitudinal end of said first wall to a profiled downstream end portion of smaller diameter than that of the cylindrical runner portion, the maximum radially expanding outer diameter of the downstream end of said first wall being 20 to 40 mm, and the length of said profiled end portion of the first wall being 10 to 30 mm, preferably 15 to 25 mm, preferably the diameter of said end portion decreasing progressively between said runner portion and said downstream end of said first wall.

More particularly, said temporary anchor element is an enteral prosthesis, said first wall of which is formed by a mesh of spiral wires, preferably metal wires. In a known manner, the radial expansion then results from the crossing of the metal wires, the angular variation of which makes it possible to vary the width of the rhombus or parallelogram of the meshes of said mesh of spiral wires.

Advantageously, said anchor element is made of a material which confers on it a said expansion by radial elasticity only at a temperature at least equal to the ambient temperature of 20° C., in particular to the temperature of the human body, said anchor element being in said radial position retracted at a temperature lower than said ambient temperature, preferably lower than 5° C. It is understood that the material in tubular form changes diameter automatically as a function of the ambient temperature.

More particularly still, said anchor element is an enteral prosthesis, said first wall of which is formed by a mesh of spiral threads, preferably made of nitinol. Nitinol is a metal alloy having properties of progressive radial expansion as a function of temperature, at a temperature greater than or equal to room temperature (25° C.), which makes it possible to keep it in retracted form at colder temperatures, in particular at 4° C. during storage. Once retracted at low temperature, it thus remains retracted for sufficient time to be able to house it in the introducer tube and to convey it into the intestine by means of said introducer. Once released in the intestine, the prosthesis gradually regains its radial expansion under the effect of a higher ambient temperature, that of the human body. In fact, for nitinol stents, the shape memory of this alloy makes it possible to modify its shape and rigidity as a function of the ambient temperature. In particular, at temperatures below 15°, nitinol becomes flexible and malleable. Thus, injecting a cold liquid solution between 0° and 15° into the vacuum chamber makes the stent malleable and facilitates its mobilization during passage through the anastomosis or a narrowing zone for example.

Advantageously, said sheath is made of biocompatible synthetic material, with a wall thickness of 0.01 to 1 mm, preferably of elastomer materials of the silicone or polyurethane type with a thickness of 0.05 to 1 mm, and preferably still having radial and longitudinal elasticity properties, and said outer sheath at least having shape memory properties and non-collision properties.

It is understood that said outer sheath, due to its elastomeric constitution, has radial and longitudinal stretchability properties similar to those of the intestinal wall, which properties are those of an elastomeric material in the form of said outer sheath, the latter having radial and longitudinal elasticity properties. These radial and longitudinal elasticity properties of the outer sheath are similar to those of the wall of the colon and allow the intestinal transit to take place correctly in said outer sheath throughout the duration of migration of the anchor element, which is a duration of at least 6 to 10 days.

The longitudinal elasticity of the elastomeric outer sheath can be greater than that of the intestine, without this posing any difficulty. On the contrary, it has the advantage of being able to be pulled over the part of the outer sheath protruding anal, so that it can be cut and retracted into the rectum. By virtue of its radial elasticity, said longitudinal end of the outer sheath remains fixed to said end of said anchor element whatever its level of radial expansion.

On the other hand, the thickness characteristics of the outer sheath combined with its elasticity give it a shape memory property. By "shape memory properties" is meant here that the elastomeric material constituting said outer sheath naturally regains its initial shape when it is deformed by folding. Given the great length of the outer sheath, these shape memory properties are important, so that the material naturally regains its longitudinal shape without creating a transit block in the event of folds in the outer sheath, which may actually occur during its migration after release of the anchor element.

"Non-sticking properties" means that the elastomeric material constituting said outer sheath has a coefficient of adhesion such that the two opposite inner wall surfaces of the outer sheath do not stick together when folded, so as not to create any resistance to the passage of gases and materials.

It is also understood that:
  said outer sheath has a resting diameter substantially equal to at least said outer diameter reduced in radial retraction of said hollow anchor element, and less than that of the resting intestine, preferably said resting diameter of said outer sheath is substantially equal to that of the resting intestinal wall, and
  said outer sheath extends downstream of the end of said anchor element to which it is attached over a length corresponding to the distance between the anchoring position upstream of said anastomosis and a position downstream preferably to the anal orifice.

In a known way, the radial expansion then results from the crossing of the wires whose angular variation makes it possible to vary the width of the diamond or parallelogram of the meshes of said mesh of spiral wires.

Preferably, and in a known manner, a stent is used whose design and shape of the mesh of the spiral wires make it possible to obtain a variation in the diameter of said stent with a minimum variation in length, preferably practically without variation in length at radial compression.

Other features and advantages of this invention will be better apparent from the description that follows, which is illustrative and not exhaustive, with reference to the following appended drawings.

FIGS. 1A, 1B and 1C represent schematic views of a protection device 5 according to the invention comprising a side view with the sheath 2 and suction tube 3 deployed downstream of the stent 1 (FIG. 1A), a frontal view of the upstream or distal end of the stent 1 mounting a lasso loop 6b (FIG. 1B) and a longitudinal cross-sectional view of the protection device 5 showing the respective positions of the stent 1, the sheath 2 and the suction tube 3, the latter opening into a chamber 4 between the wall of the stent and the inner part 2a of the sheath 2.

FIG. 2 shows the different parts of a dismantled introducer device 10.

FIG. 2A shows the introducer device 10 with the first guide tube 12 inserted into the upstream part of the intestine 100a.

FIGS. 3A and 3B show a detail of a deformable pusher rod 15b with a spiral shape in side view (FIG. 3A) and in front view of one of its ends (FIG. 3B).

Figure 2:
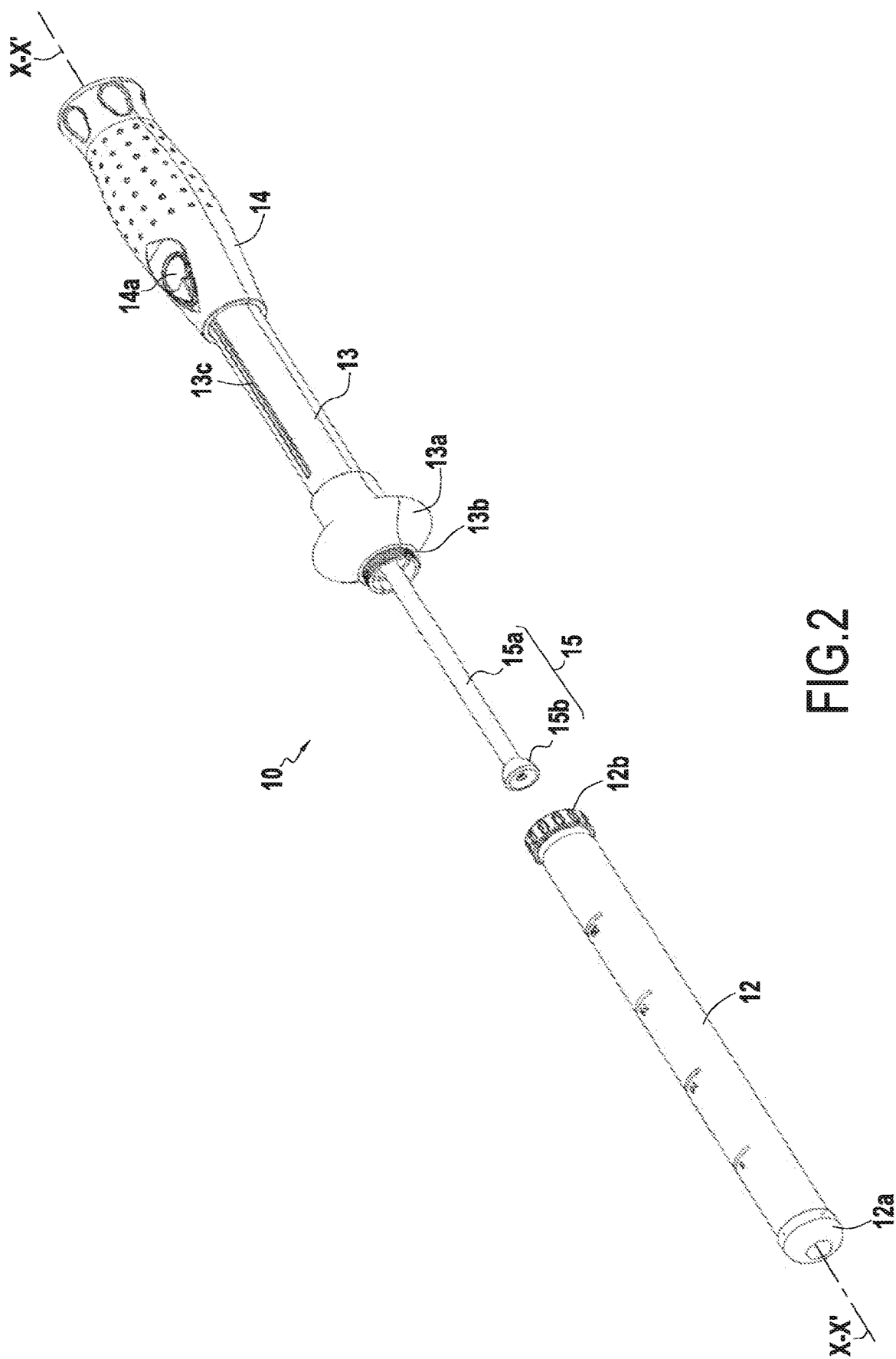
FIG. 2B shows the release of the stent from the first guide tube 12 by the thrust of the pusher rod 15 (not visible in FIG. 2B).

FIGS. 4A to 4D show the different steps of placing an anvil 8 and stapling an anastomosis 101 between the upstream part 100a and the downstream part 100b of the intestine with a stapler 9 cooperating with an anvil 8.

FIGS. 5A-5B, 6 and 7A-7D relate to the embodiment of Example 1.

Figure 5A:
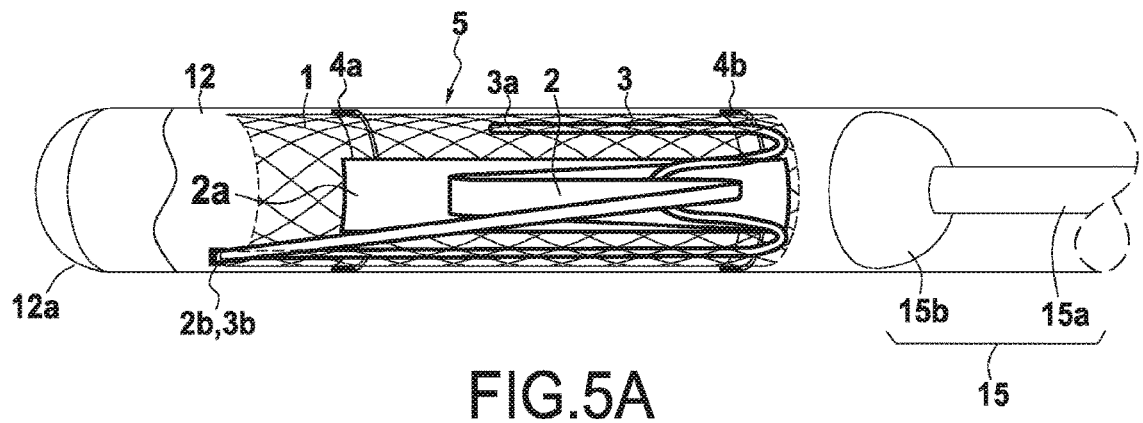
Figure 5B:
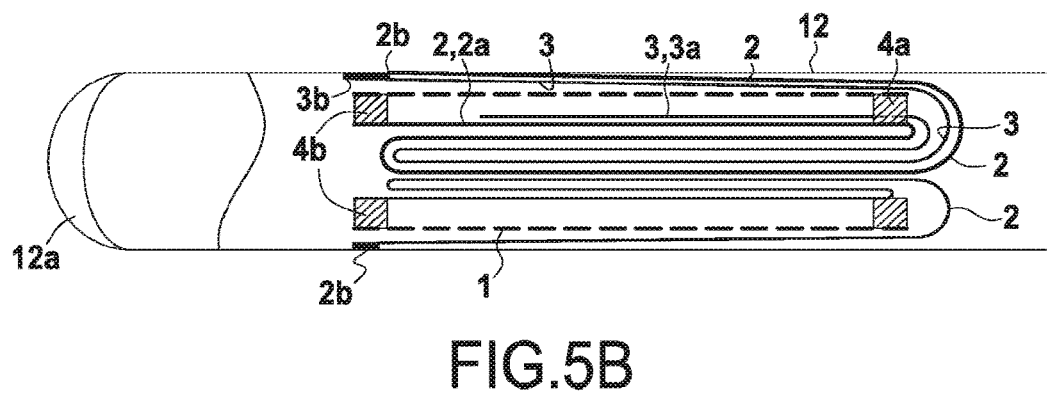

FIGS. 5A and 5B show two variants in schematic sectional views (partially exploded for FIG. 5A) of a protective device 5 with the stent compressed at the distal end of the first tube 12 in which the sheath 2 and the suction tube 3 are folded inside the stent, their downstream ends being stuck to the distal end of the first tube, the protective device 5 being ready to be expelled by the stop 15b of the pusher 15 out of the first guide tube 12.

Figure 6:
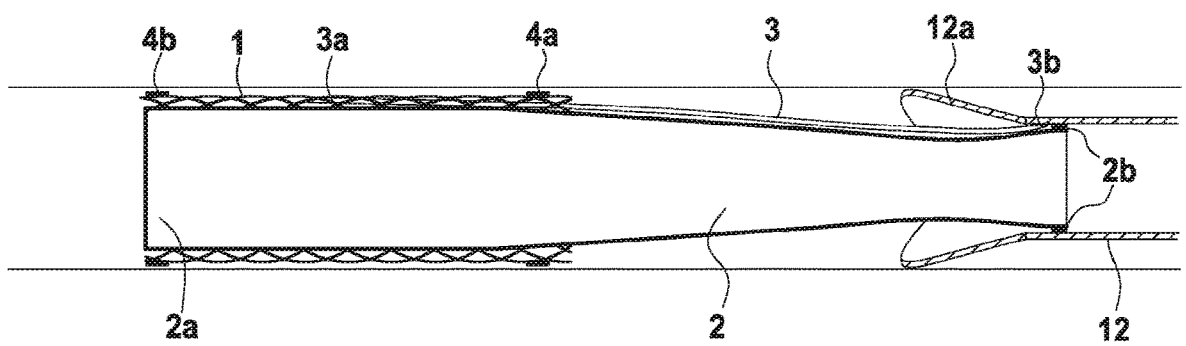

FIG. 6 schematically shows stent 1 released externally with the first guide tube 12 separated from the rest of the introducer and emptied from the push rod after release of the stent and deployment of the sheath 2 and the suction tube 3 downstream of the stent 1 due to the removal of the first guide tube 12 to which they are attached.

Figure 7A:
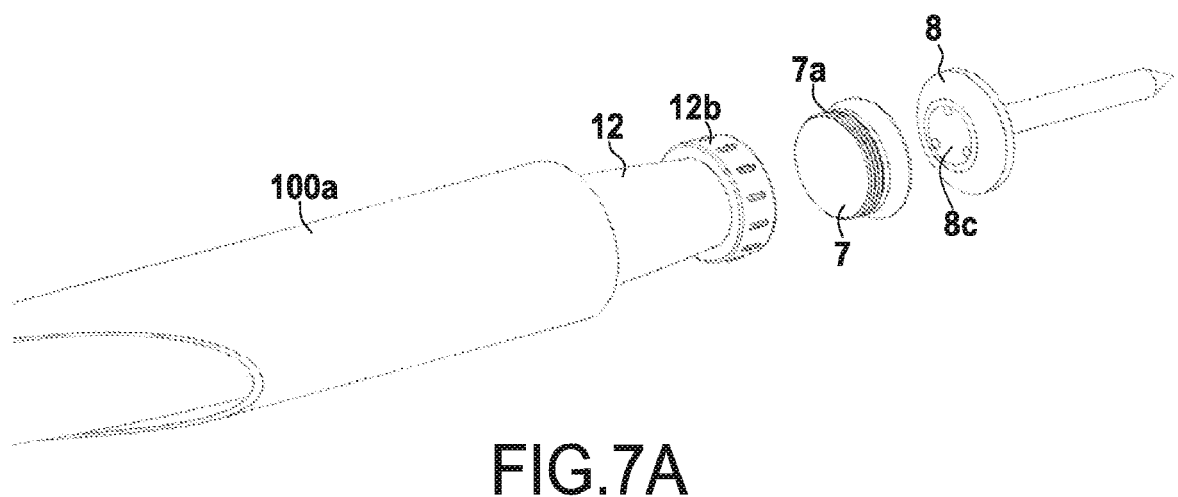
Figure 7B:
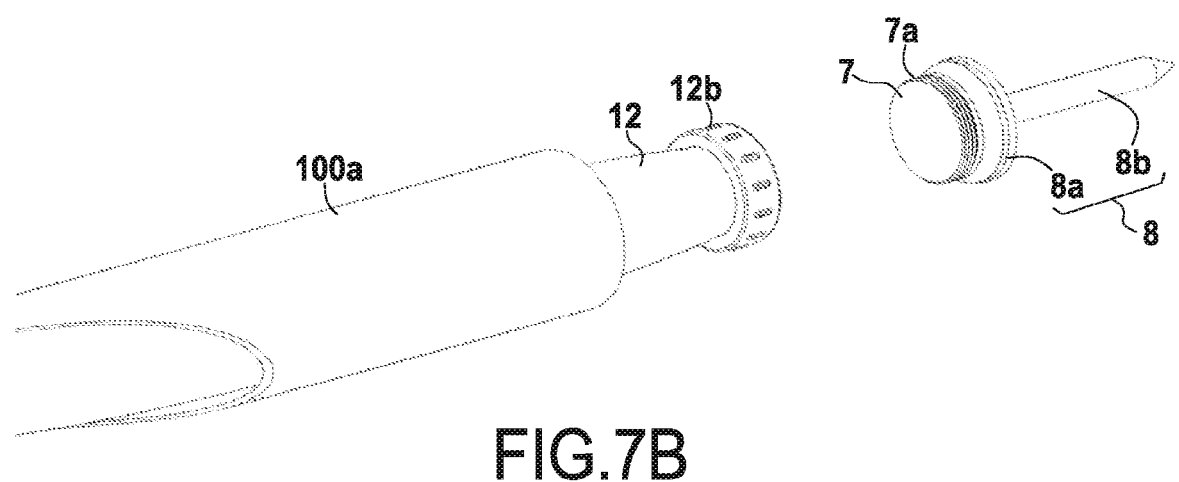
Figure 7C:
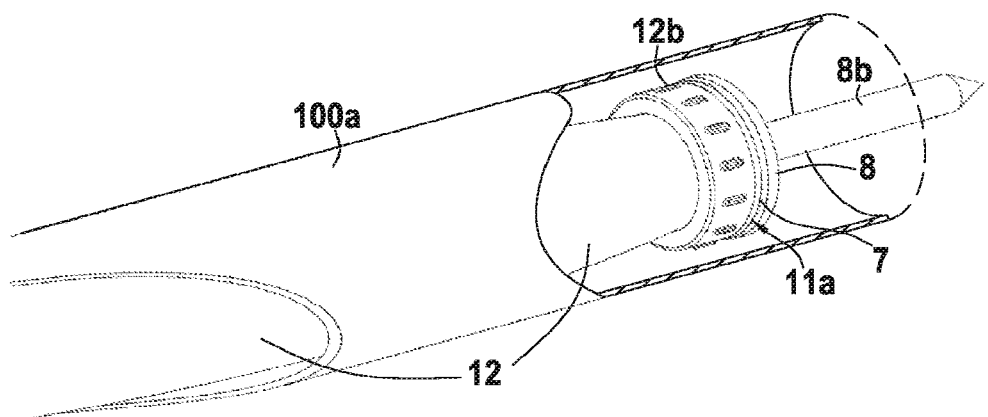

FIGS. 7A to 7C show the different steps for placing the anvil at the proximal end of the first guide tube 12 before anastomosis is performed.

Figure 7D:
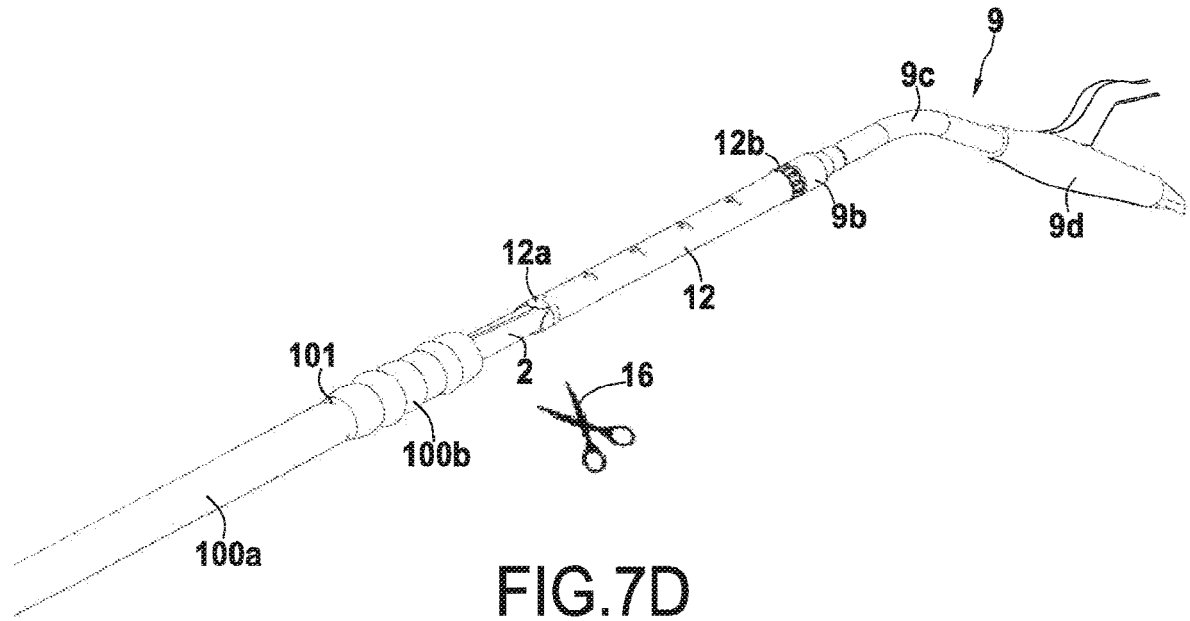

FIG. 7D shows the removal of the stapler attached to the first tube 12 allowing the deployment of the sheath 2 after anastomosis.

FIGS. 8A-8B, 9A-9B, 10A-10C and 11A-11B represent the embodiment of Example 2.

Figure 8A:
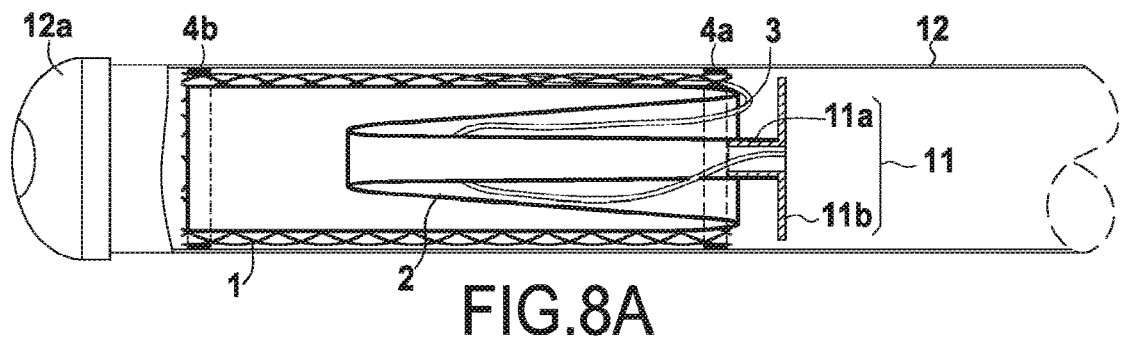
Figure 8B:
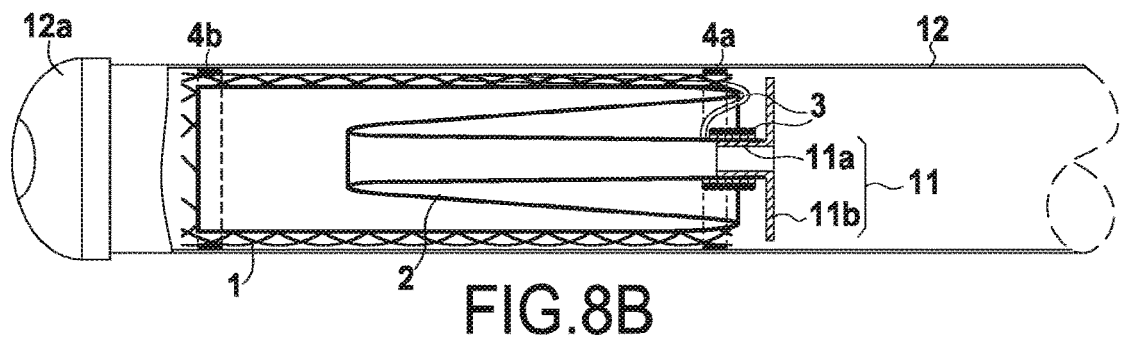

FIGS. 8A and 8B show two alternatives for attaching the suction tube 3 and the sheath 2 to a first connecting piece 11 downstream of the stent 1 and independent of the first guide tube.

Figure 9A:
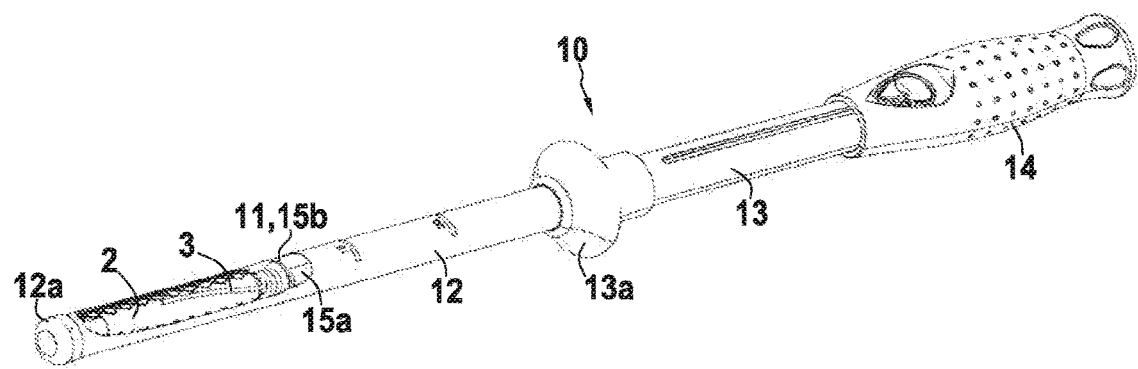
Figure 9B:
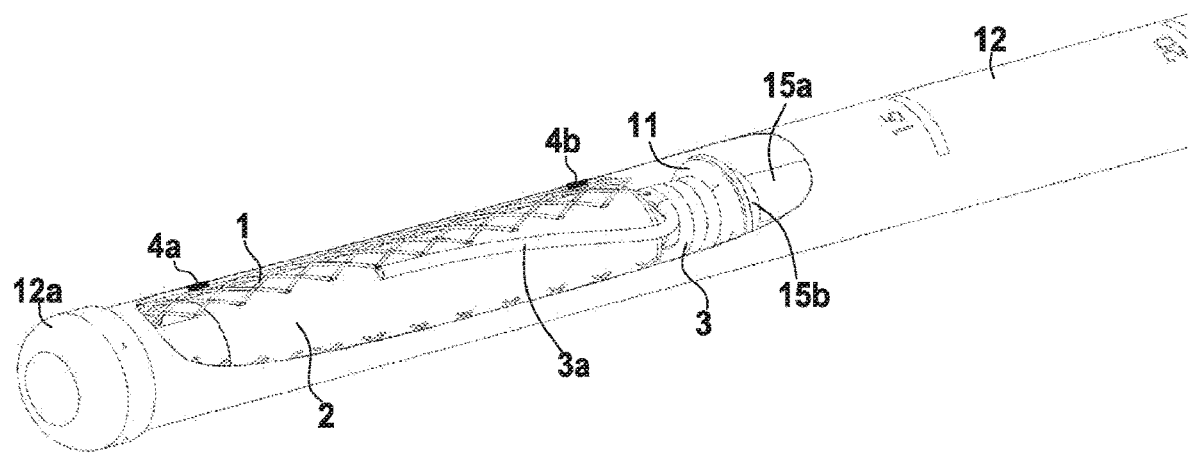

FIGS. 9A and 9b show a protective device 5 with the stent 1 at the distal end of the first guide tube 12 and the sheath 2 and the suction tube 3 attached to an adapter 11 itself reversibly attached to the stop 15b of a pusher 15.

Figure 10A:
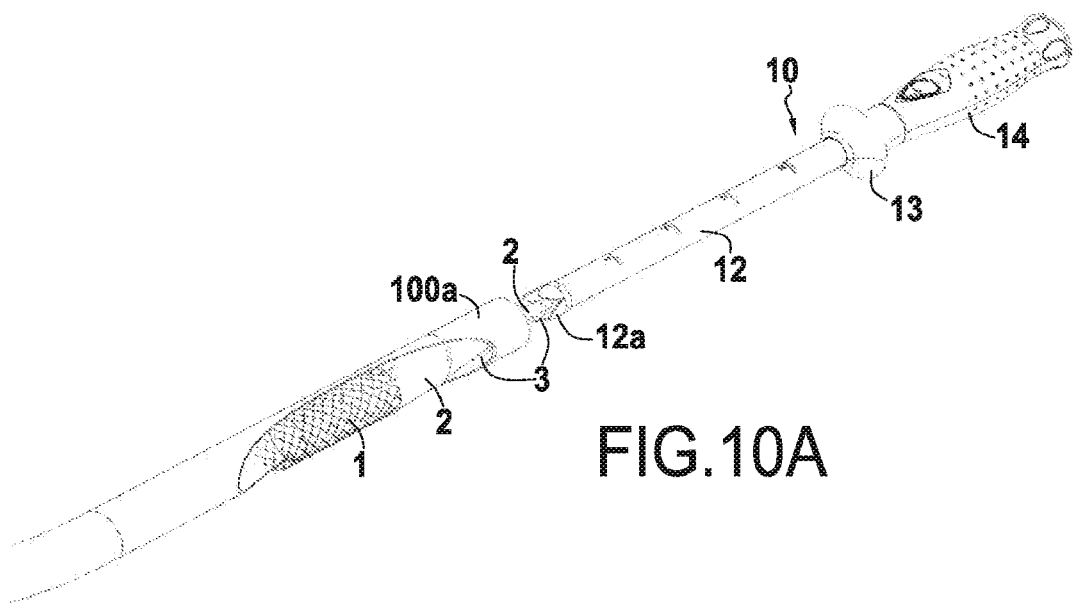
Figure 10B:
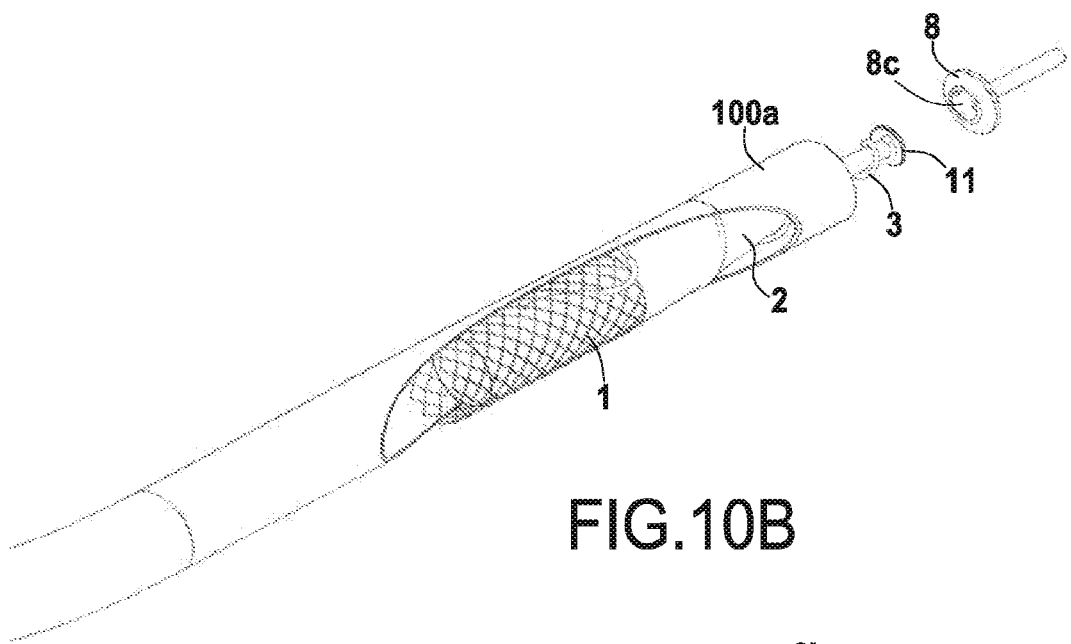
Figure 10C:
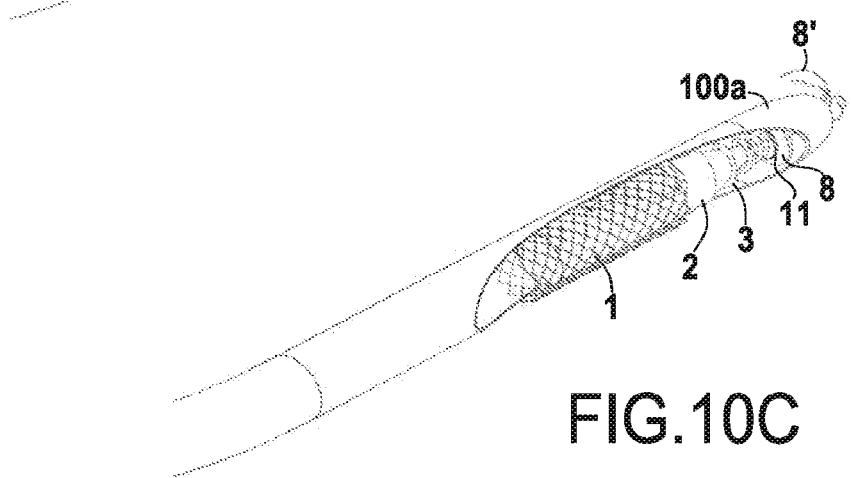

FIGS. 10A, 10B and 10C show different steps of the removal of the introducer 10 including the first guide tube 12 after release of the stent 1 and partial deployment of the sheath 2 and the suction tube 3 connected to the first connecting piece 11. FIG. 10B shows the approach of the anvil 8 to the first connecting piece 11. FIG. 10C shows the fixation of the anvil 8 in the upstream bowel 10a before anastomosis is performed with the stapler 9.

Figure 11A:
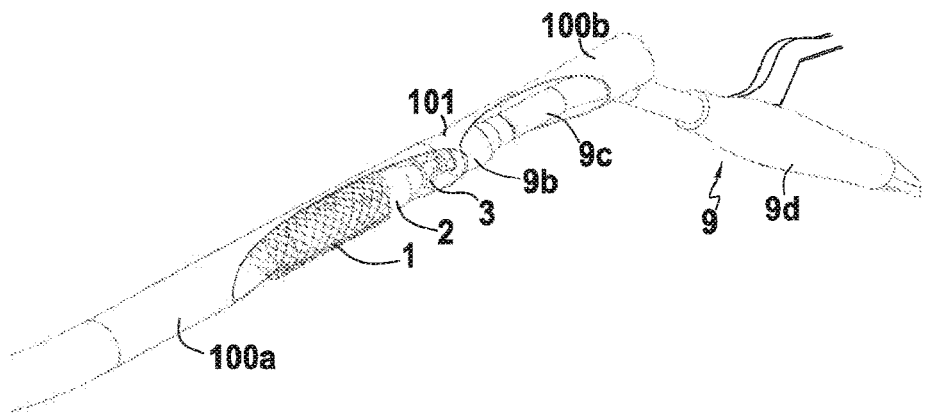
Figure 11B:
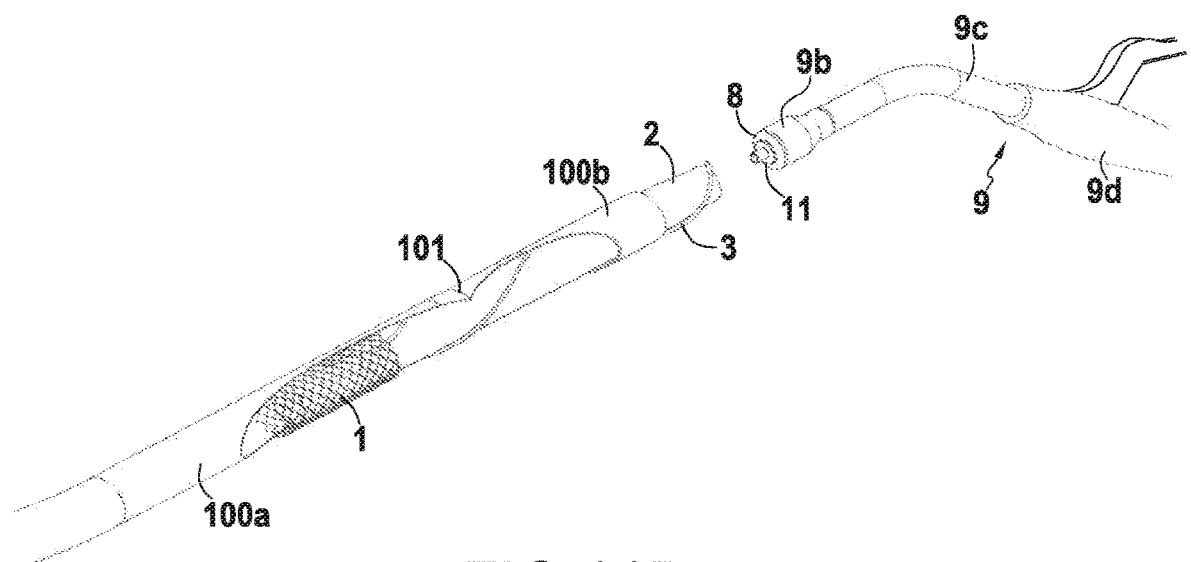

FIGS. 11A and 11B show the stapler 9 with the anvil 8 attached to the downstream ends of the sheath 2 and the tube 3 when performing the anastomosis 101 (FIG. 11A) and after removal of the stapler and separation from the first connecting piece 11 after carrying out the anastomosis 101 (FIG. 11B). In the two embodiments of Examples 1 and 2 below, an anastomosis protection device 5 of FIGS. 1A-1C of the type described in WO2013/014353 packaged in a part of an introducer device as described below with reference to FIGS. 2, 2A-2B and 3A-3B is used to perform an anastomosis described with reference to FIGS. 4A-4C.

The anastomosis protection device 5 comprises an anchor element consisting of a stent 1 whose inner wall is covered by a flexible inner sheath 2a delimiting an annular chamber 4 between annular seals 4a-4b which seal between the inner sheath 2a and the perforated wall of the stent. The inner sheath 2a constitutes a sealed film forming a flexible tubular wall and is extended by a flexible outer sheath 2 extending outside said anchor element in the longitudinal direction of said stent. The entire length of the cylindrical inner surface of the inner wall of the stent is thus doubled by an independent sealing layer forming an inner sheath 2a, only the longitudinal ends of said inner sheath 2a being attached in a sealed manner to said anchor element 1 by means of the elastomeric annular seals obtained by fusion at each said longitudinal end of said inner sheath.

As is well known, the stent 1 advantageously includes flared flanges at its upstream and downstream ends as shown in patent WO 2013/014353.

It is understood that the inner sheath 2a is not overstretched so as not to stiffen the stent, so that the distance between said inner sheath 2a and the maximum external diameter of the stent is preferably 0.2 to 10 mm, preferably 1 to 5 mm, and the space between said inner sheath 2a and said stent wall defines a chamber called the vacuum chamber 4.

The protective device 5 according to the invention further comprises a flexible or semi-rigid tube called suction tube 3 extending externally downstream of said stent and opening into the vacuum chamber 4 between the inner sheath 2a and the wall of the stent 1, an upstream part of the suction tube 3 comprising multiple perforations, extends substantially over the entire length of said chamber 4 in the longitudinal direction XX of the device. The suction tube 3 opens into said vacuum chamber by passing in a sealed manner through the elastomeric annular seal at the downstream end of the inner sheath 2a when the tube 3 is introduced through the anal orifice. Said suction tube 3 and said outer sheath 2 extend outside said stent from the same downstream end of said stent.

The suction tube 3 is used to inject or suck air into the chamber 4 to draw the intestinal wall 100a against the outside of the stent 1, and more generally to modify the anchoring characteristic of the stent 1 in relation to the intestinal wall 100a.

The portion 3a of the suction tube 3 inside chamber 4 can be bonded to the inner side of the stent 1 or to the outer side of said outer sheath 2.

Alternatively, the outer sheath 2 can be attached at its upstream end to the same elastomeric fusion joint 4a-4b or can be attached to the outer face of the downstream longitudinal end of the stent by overlapping it over a short portion of its length (not shown in the figures).

The stent of the type made by spiral meshing of nitinol metal wires giving it radial elasticity properties so that it can be radially compressed in a retracted position and adopt a said maximum radial expansion position after release of the radial compression such that said first multi-perforated wall has a first external diameter which can be varied in a controlled manner between:
 a minimum outer diameter in said retracted radial position of said first wall of 16 mm, and
 a maximum external diameter at said maximum radial expansion position of said first wall of 37 mm.

The dimensional data for the diameters given above correspond to appropriate dimensions for anchoring the device against the mucous membrane of the inner wall of the intestine 10 at various positions between including the rectum. The stent is made of a mesh of 0.32 mm nitinol wires braided at an angle of 30° and has a diameter of 34 mm at the running part and 37 mm at its flared ends, a length of 100 mm.

The proximal and distal parts of the stent, and where applicable the flanges (not shown), are each equipped with a lasso wire 6a, 6b to reduce the diameter of the stent in traction. These lassos wires 6a, 6b can be grasped with a dedicated clamp or hook inserted via an endoscope.

Said sheath 2 extending outwards has a length covering the distance between the anastomosis and the upstream anchorage site, i.e. at least 10 cm.

The sheath 2 is made of biocompatible synthetic material, radiopaque, in particular TPU 90 AE with 18% $BaSO_4$, its dimensional characteristics are: thickness of 100 μm, resting length of 400 mm (excluding the internal part of the stent), and external diameter of 37 mm.

Said suction tube 3 made of Pebax® elastomeric material (ARKEMA, France) is attached to the stent by the same fusion joints 4a-4b as the inner sheath 2a at the ends of the stent and has a length covering at least the distance between the anastomosis and the upstream anchorage site, i.e. at least 10 cm. Its characteristics are length of 500 mm±2 mm; thickness of 05 mm; internal diameter of 2 mm; and external diameter of 3 mm.

The outer free longitudinal end of said suction tube 3 is reversibly connected to a connecting piece having a shut-off device consisting of an anti-backflow valve with a device for indicating the vacuum content in the chamber 4.

The stent 1, the outer sheath 2 and the injection suction tube 3 are packaged in a semi-rigid plastic deformable tube 11 made of elastomer material, hereinafter referred to as the first deformable guide tube 12. This first guide tube 12 is part of an introducer device 10 described below.

The stent is introduced in retracted form (radially compressed) at the upstream distal end of said first deformable guide tube 12, said outer sheath 2 and said suction tube 3 being arranged folded back on themselves in several superimposed layers partly inside the stent and partly inside the first guide tube 12 of the introducer 10.

The fixing of the downstream ends of the outer sheath 2 and the suction tube 3 are different in the two embodiments of Examples 1 and 2, the first guide tube 11 having distinctive characteristics of implementation between the two embodiments which will be explained below. The stent is retained inside the first guide tube 12 by a device called a tulip 12a formed of cut-out tabs blocking the passage of the upstream or distal end of the first guide tube 12, which prevents the stent from coming out in the absence of a thrust by the pusher stop described below, said tabs being elastically deformable under the effect of a said thrust enabling the stent to be expelled outside the first guide tube 12.

The introducer device 10 comprises a handle 14 which is attached to a second rigid tube 13 also referred to as the second guide tube, terminating at its distal end in a connecting part 13a with the first guide tube 12. This connecting part 13a is convexly curved externally and is larger in diameter than the first deformable guide tube 12 and second rigid guide tube 13 to serve as a stop.

A means of actuation by pressure or push button 14a on the handle 14 controls the longitudinal translation of a pusher rod 15a ending in a pusher stop 15b of a pusher 15. The pusher rod 15a and the pusher stop 12b are arranged coaxially inside the second rigid tube 13. The proximal end of the pusher rod 15a cooperates with the push button 14a on the handle 14. The distal end of the pusher rod and the pusher stop are capable of expelling the stent out of the upstream end (distal end) of the first deformable guide tube 12 by actuation of the pusher rod and pusher stop in relative transaction inside the first deformable guide tube 12.

The pusher stop 15b is initially positioned just downstream of the stent inside the first deformable guide tube 12.

In the two embodiments of Examples 1 and 2 below, the first deformable guide tube 12 of the introducer containing the protective device 5 radially compressed as described above is introduced abdominally into the upstream part 100a of the intestine which has been sectioned at the site 101 where an anastomosis is to be carried out. In this case, the implantation site is located at a distance of 10 cm to 20 cm upstream of the anastomosis.

At this stage, the stent as well as the outer sheath 2 and the suction tube 3 are still packed inside the stent, at least in part, and inside the first deformable guide tube 12. In its initial form, closed and housed in the introducer, the stent 1 has a diameter reduced to the diameter of the deformable guide tube 11, i.e. in particular 10 mm.

Once released outside the first deformable guide tube 12 into the lumen of the upstream intestine 100a, the stent gradually regains its final diameter. It can be temporarily held in place by the surgeon, who pinches the stent through the walls of the intestine. At least part of the introducer is then removed without the outer sheath 2 and the suction tube 3 being unfolded and deployed downstream of the stent. However, these elements can be partially deployed up to the anastomosis zone (the stent is released 10-20 cm above this zone). This is to allow the anastomosis to be performed before the outer sheath and suction tube is unfolded and deployed more fully downstream of the stent. The release of the stent outside the first deformable guide tube 12 into the lumen of the intestine, with the stent gradually regaining its final diameter, is done at this stage, ideally before the anastomosis is performed.

Said first deformable guide tube 12 has an internal diameter of 10 mm, an external diameter of 17 mm and a length of at least 70 cm, preferably at least 100 cm with a graduation every 5 cm. It is made of Pebax® material to limit friction during insertion and removal.

The second rigid tube 13 has a length of 176 mm including the connecting part 13a curved convex with a protruding diameter of 53 mm forming a stop and a length of 46 mm. The second rigid tube 13 has a central guide groove 13b controlling the translation of the inner pusher rod.

The shaft 15a of said pusher 15 is made of stainless steel and has a length before the stop 15b of 487 mm. The rod 15a is a rod formed of a wire of 1.4 mm diameter wound helically along a virtual longitudinal axis XX' with adjoining turns, the diameter of the adjoining turns forming a deformable rod with an external diameter of 7 mm. Such a rod 15a can be deformed in curvature to allow a bend of up to 90°.

Figure 4C:
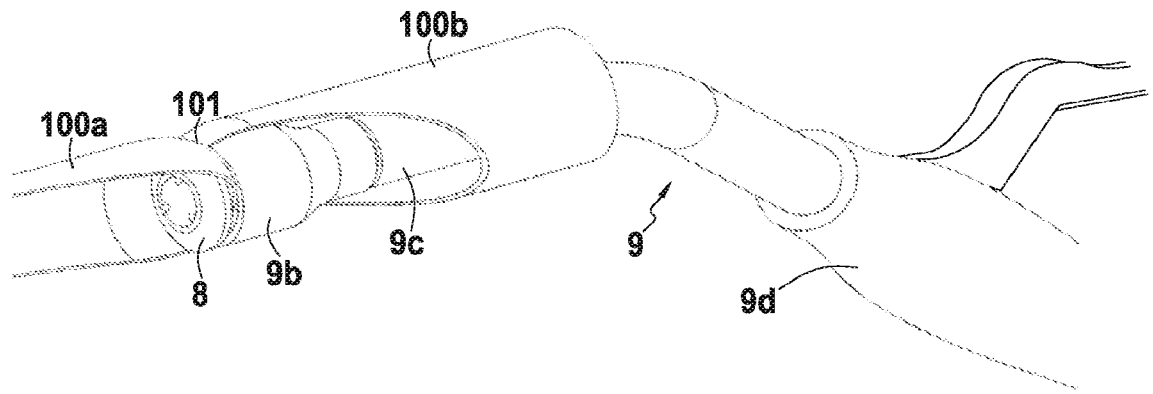
Figure 4D:
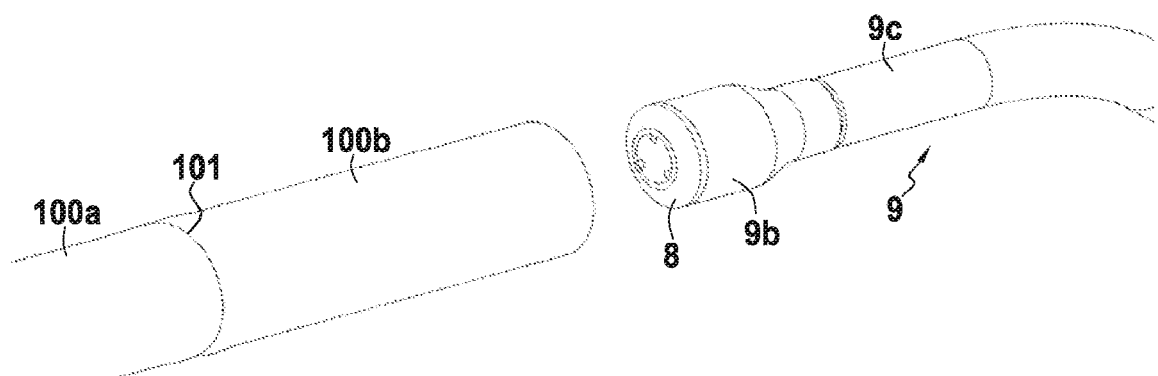

FIGS. 4A to 4D show the various steps involved in making an anastomosis with an anvil 8 and a circular stapler 9. An anvil 8 is inserted into the upstream part 100a of the intestine just upstream of the anastomosis site 101 at the free end of the upstream intestine part 100a. Then, ligation of this free end of the intestine is performed with a purse string 8' around a shaft 8b behind the circular cross-section part 8a of the anvil 8. Then, a stapler 9 is introduced into the downstream part 100b of the intestine, which comprises a hollow body 9b of circular cross-section intended to cover the circular part 8a of the anvil and containing an axial finger 9a capable of cooperating in an axial hollow (not shown) in the shaft 8b, making it possible to thus to engage the stapler 9 to cooperate with the anvil 8 to perform stapling at the anastomosis 101 between the upstream part of the intestine 100a and the downstream part 100b of the intestine before the anvil 8—stapler 9 assembly is removed from the intestine as shown in FIG. 4D. In FIGS. 4B to 4D, the stapler 9 is shown downstream of a downstream segment of the intestine as a schematic illustration with the understanding that the stapler 9 is actually introduced initially via the rectum. In particular, an EEA® stapler from the company COVIDIEN (France) is used, comprising a handle 9d and a deformable duct 9c capable of following the curves of the intestine to connect the handle 9d to the stapler part 9b which cooperates with the anvil 8 to control stapling.

More precisely, the following successive steps are carried out:
1) the diseased intestine is resected using a linear stapler, resulting in closure 100d and sectioning of the intestine downstream 100b of the diseased intestine segment;
2) a purse string 8' is applied to the intestine located upstream of the diseased segment before cutting it;
3) the anvil 8 of a circular stapler is inserted into the upper intestine 100a and the purse string 8' is tightened and knotted around its central axis 8b;
4) the body 9b of the circular stapler is inserted into the downstream intestinal segment 100b (through the anal orifice) up to its closed end 100d;
5) the central axis 9a of the circular stapler is pushed out through the walls of the downstream intestine by penetration;
6) the central axis 9a of the circular stapler is connected to the central axis 8b of the anvil;
7) the 2 pins 8a-9a joined together are inserted into the body of the stapler resulting in the anvil section being attached to the body section of the stapler; and
8) the walls of the 2 intestine segments 100a and 100b joined together in 101 are stapled and sectioned in a circular section. The end stop 15b of the pusher is made of Pebax® material and has a diameter and thickness in the longitudinal direction of the rod of 10 mm.

In the two embodiments of Examples 1 and 2, the outer sheath 2 and the suction tube 3 are unfolded and extended downstream of the stent by removing the anvil after stapling has been performed.

Removal of the protective device should ideally take place after healing of the anastomotic area, the standard duration of which is 14 days.

Withdrawal can be done in 2 ways:
a) removal by reversal during an endoscopic procedure, In this case, a lasso loop 6b at the distal (or upstream) end of the stent is grasped with forceps. This has the effect of reducing the diameter of the stent. When the stent is fully retracted radially, it is then possible to turn the stent over by pulling on the lasso wire, which causes the stent to flip or invert, while gradually pulling it away from the tissue.
b) the second method of withdrawal involves the use of a withdrawal tube. In this case, the outer sheath and the suction tube are inserted into a withdrawal tube. A lasso loop 6a located at the proximal (or swallowed) end of the stent is grasped with forceps (this is guided by the use of an endoscope). This has the effect of reducing the diameter of the stent (by radial retraction). When the stent is fully retracted, it is then possible to slide it into the removal tube. Advancing the retraction tube allows the tissue to be loosened and the stent to be collected atraumatically. The withdrawal tube containing the stent is then removed by the anal route.

In the two embodiments of Examples 1 and 2, the connection configuration of some of the components of the introducer between themselves or with the protection device 1 are different and in particular the downstream longitudinal ends of the outer sheath 3 and of the suction-injection tube 4 are connected to an element of the introducer device which is different. The downstream ends of the outer sheath 2 and of the suction tube 3 are attached to the distal end of said first guide tube 12 in the embodiment of Example 1 and to a first connecting piece 11 capable of being reversibly attached to the stop 15b of the pusher in the embodiment of Example 2.

Example 1

In FIGS. 5A, 5B, 6 and 7A-7B, a first embodiment of a complex device according to the invention is shown in which the downstream ends of the sheath 2 and of the suction tube 3 are fixed in 2b-3b near the upstream or proximal end of the first deformable tube 12.

In FIG. 5A, the sheath 2 and the suction tube 3 are folded inside the stent 1 and protrude downstream of the stent beyond the seal 4b to join the upstream end of the first guide tube 12 from the outside, with the ends of the sheath 2 and of the suction tube 3 bonded against the inner wall of the first guide tube 12 in 2b-3b near the upstream or proximal end of the first guide tube 12.

FIG. 5B schematically shows an embodiment in which there are several folds of the sheath 2 and of the suction tube 3 inside the stent 1, which sheath 2 and suction tube 3 join the inner wall of the first deformable tube 12 by being interposed between the outer wall of the stent 1 and the inner wall of the first guide tube 12. In FIG. 5B, the positioning of the stent 1 inside the first guide tube 12 has been schematically illustrated by over-exaggerating the space between the stent 1 and the inner wall of the first guide tube 12 to show the positioning of the sheath 2 and the suction tube 3 outside the stent 1, but in reality the stent 1 is in radial compression pushing against the inner wall of the first guide tube 12 with the sheath 2 interposed and wedged between them at this initial stage.

In this embodiment, the stop 15b of the pusher 15 has a cross-sectional diameter slightly larger than the diameter of the stent and is therefore able to expel the stent towards the exit of the proximal end 12a of the first deformable guide tube 12 under the effect of the translational thrust of the pusher 15 actuated at the handle 14 of the introducer device 10.

FIG. 6 shows the complete deployment of the sheath 2 and the suction tube 3 downstream of the stent 1 when, after completion of the anastomosis described below in conjunction with FIGS. 7A-7D, the situation is as shown in FIG. 7D with the first tube 12 removed from the bowel. In practice, this removal takes place until the stapler exits through the anal orifice. At this point, as shown in FIG. 7D, the sheath 2 and the suction tube 3 are cut with scissors 16 to separate them from the complex assembly of the first tube 12, which is attached to the stapler 9 by the second connecting piece 12b.

In this embodiment, as shown in FIGS. 7A-7C, the proximal end of the first deformable guide tube 12 in fact comprises a part called second connecting part 12b comprising an internal thread capable of screwing cooperation with a complementary thread element 7a of a part called adapter 7, the latter being capable of being fixed for example by reversible bonding with the front face 8c of the anvil 8.

Figure 2A:
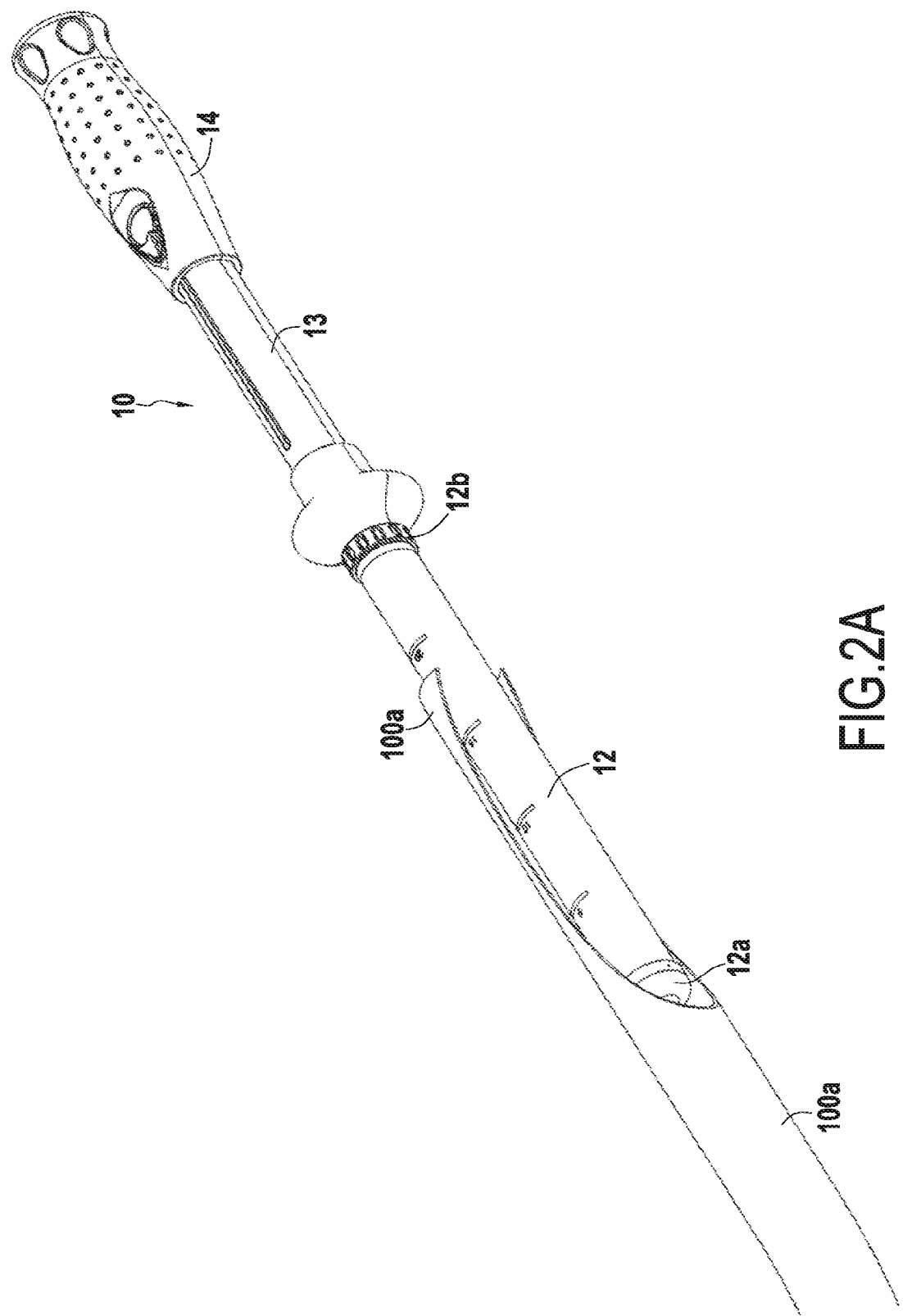
Figure 2B:
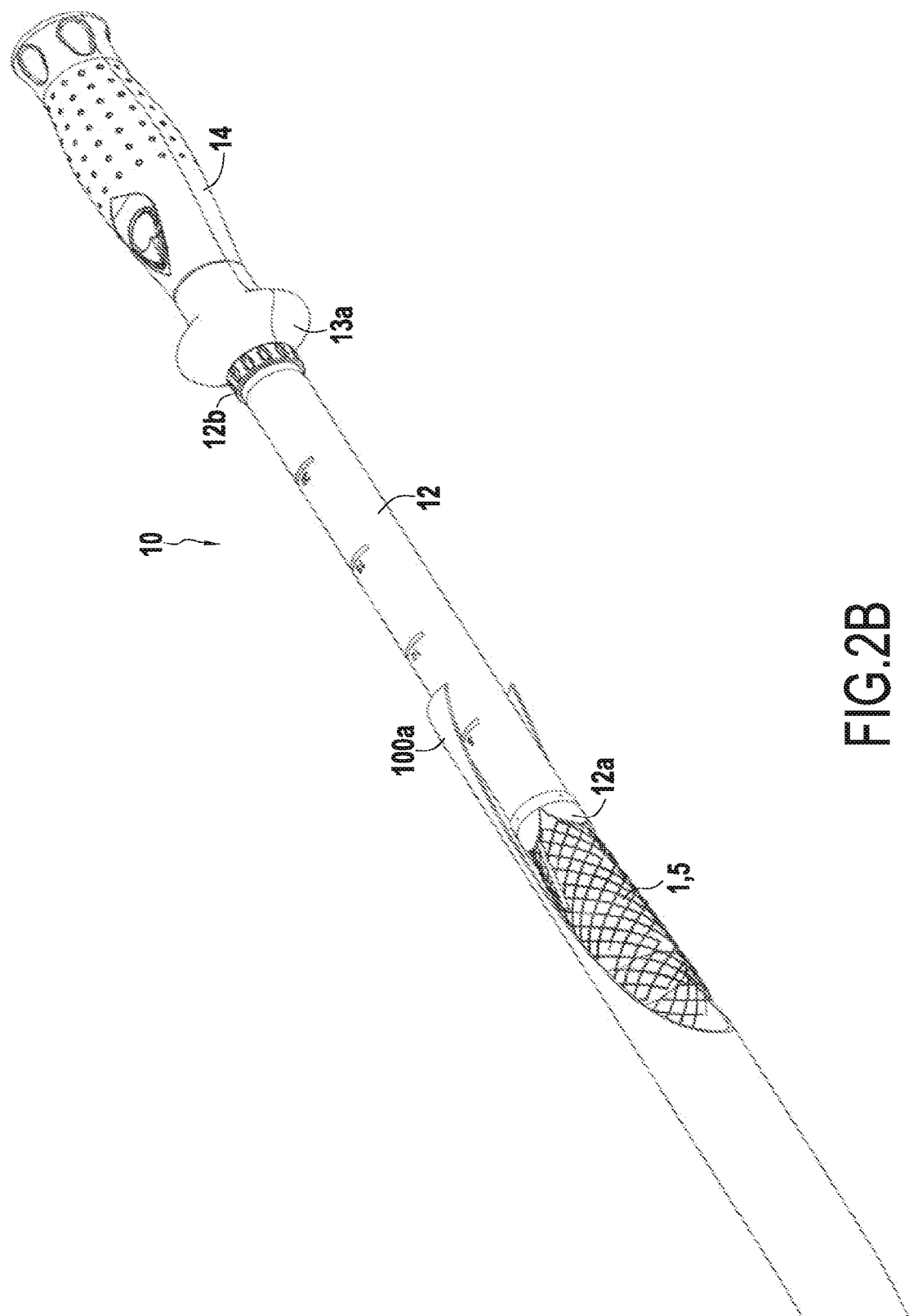

In this embodiment, the second connecting piece 12b initially serves to receive the introducer 10 as shown in FIG. 2 by screwing the complementary threaded element 13b to the distal end of the second rigid guide tube 13 to arrive at the configuration of FIGS. 2A and 5A in which the stop 15b arrives near the downstream end of the stent 1 inside the first guide tube 12. At this point, the pusher rod 15a is actuated by relative translation of the second rigid guide tube 13 with respect to the handle 14 through an indentation 13c along the second rigid tube 13. This translation is controlled by actuation of the pusher rod 14a, to expel the stent 1 out of the first guide tube 12 as shown in FIG. 2B. At this point, the second connecting piece 12b is located approximately at the free end of the upstream part 100a of the bowel and is therefore in position to receive the anvil 8 via the interposition of an adapter 7 as shown in FIGS. 7A to 7C. The anastomosis is then performed with the stapler 9 as described with reference to FIGS. 4A to 4C. Then, the first guide tube 12—anvil 8—stapler 9 is removed from outside the patient at the anal orifice to the configuration shown in FIGS. 6 and 7D. In FIG. 7D, the stapler is shown downstream of a downstream segment of the intestine 100*b* as a schematic illustration with the understanding that the stapler 9 is actually removed from the intestine via the rectum.

In this embodiment, preferably, the sheath 2 and the suction tube 3 are not attached directly to the end of the deformable tube 12 in 2*b* and 3*b* but via a tie such as a suture (not shown).

Example 2

FIGS. 8A-8B, 9A-9B, 10A-10C and 11A-11B illustrate the distinguishing features of a second embodiment of a complex device according to the invention.

In this second embodiment, the downstream ends of the sheath 2 and the suction tube 3 are attached to a first connecting piece 11 positioned just outside the downstream end of the stent 1.

FIGS. 8A and 8B show two variants of the arrangement of the sheath 2 and of the suction tube 3 inside the stent 1. In both cases, the sheath 2 and the suction tube 3 are initially arranged inside the stent. In the first preferred variant of FIG. 8A, the suction tube 3 and the sheath 2 are simply attached to a tubular part 11*a* at the distal end of the first connecting piece 11 and folded inside the stent 1, with the suction tube 3 not being wound onto the tubular part 11*a* as in the second variant of FIG. 8B. The various stages of implementation of the complex device according to the invention in this second embodiment are illustrated in relation to this second variant of FIG. 8B but can be transposed to the variant of FIG. 8A. The tubular part 11*a* of the connecting piece 11 initially fits inside the stent 1 at its downstream end and the larger diameter part lib serves as a support for the stop 15*b* of the pusher rod for the insertion phase and then serves for the reversible fixing of the connecting piece 11 against the front face 8*c* of the anvil 8 for the stapling phase and making of the anastomosis.

In this embodiment, the complex device according to the invention comprising the assembly of the protective device 5 and the first connecting piece 11, which assembly is independent of the first guide tube 12. Thus, the first guide tube 12 can be irreversibly fixed at the connection piece 13*a* to the distal end of the second rigid guide tube 13 of the introducer 10 as shown in FIG. 9A.

FIGS. 9A and 9B show that initially the stop 15*b* at the distal end of the pusher rod 15*a* is applied against the flat proximal face bib of the first connecting piece 11 to expel the stent 1 out of the first guide tube 12 by translation of the pusher rod 15. Then, as shown in FIG. 10A, the introducer 10 is removed from the upstream bowel section 100*a* to leave the first connecting piece 11 at the anastomosis site 101. It is advantageous that the stop 15*a* is reversibly glued to the first connecting piece 11 to allow partial unfolding of the sheath 2 and the suction tube 3 during the preliminary partial removal of the introducer 10 until the part 11 reaches the anastomosis site as shown in FIG. 10B. At this point the anvil 8 is reversibly fixed against the first connecting part 11, for example by reversible bonding. The anastomosis is then performed as in example 1 and as shown in FIGS. 4A to 4C until the situation shown in FIGS. 11A and 11B is reached in which the assembly attached to the first connection piece 11—anvil 8—stapler 9 is removed to deploy the sheath 2 and the tube 3 completely downstream of the stent 1 and downstream of the anastomosis 101 to the anal orifice where the sheath 2 and the suction tube 3 are separated from the first connection piece 11 with the scissors 16. In FIGS. 11A-11B, the stapler 9 is shown downstream of a downstream segment of intestine 100*b* schematically with the proviso that the stapler 9 is actually inserted and removed from the intestine via the rectum with the handle 9*d* remaining outside the rectum.

In an example of a simplified version (not shown), the flexible sheath 2 and two suction tubes 2 are initially arranged within said first tube 12 but entirely outside the stent, downstream of the stent said stent being held in radial compression within said first guide tube, and the two suction tubes 2 being arranged so as to be able to extend diametrically opposite to said stent and outside the sheath.

What is claimed:

1. A device for introducing an implantable device into an intestine to protect an anastomosis site, the device comprising:
    a first guide tube configured to hold the implantable device therein in a radially compressed state, the first guide tube comprising a distal end configured to be introduced through an anal orifice into the intestine to a position upstream of the anastomosis site;
    a second guide tube positioned proximal to the first guide tube;
    a stop between the first guide tube and the second guide tube, the stop having a diameter larger than that of the first guide tube and the second guide tube; and
    a handle positioned, in a delivery state, proximal to the second guide tube, wherein a distance between the first guide tube and the handle is configured to be reduced to release the implantable device out of the distal end of the first guide tube at the position upstream of the anastomosis site for implanting the implantable device for protecting the anastomosis site.

2. The device of claim 1, wherein the second guide tube is configured to be moved into the handle when the distance between the first guide tube and the handle is reduced.

3. The device of claim 1, wherein the second guide tube comprises a guide groove configured to control translation.

4. The device of claim 1, wherein the distal end of the first guide tube comprises cut-out tabs configured to block the distal end of the first guide tube.

5. The device of claim 4, wherein the cut-out tabs are elastically deformable to permit the implantable device to be deployed therethrough.

6. The device of claim 5, wherein the cut-out tabs form a tulip configuration.

7. The device of claim 1, wherein the handle comprises an actuator configured to control longitudinal translation.

8. The device of claim 7, wherein the actuator comprises a button on the handle.

9. The device of claim 1, further comprising a pusher disposed within the first guide tube, the pusher configured to cause the implantable device to be released out of the distal end of the first guide tube when the distance between the first guide tube and the handle is reduced.

10. The device of claim 1, wherein the implantable device comprises a stent coupled to a sheath, the stent configured to expand upon release from the distal end of the first guide tube to anchor the implantable device at the position upstream of the anastomosis site such that the sheath protects the anastomosis site.

11. The device of claim 10, wherein the implantable device comprises at least one suction tube configured to permit application of suction at the stent to increase anchoring force at the stent.

12. The device of claim 11, wherein the at least one suction tube comprises two suction tubes, each suction tube being connected to a vacuum chamber between the stent and the sheath for maintaining vacuum in the vacuum chamber.

13. The device of claim 1, wherein the device is configured to introduce the implantable device before an anastomosis is carried out at the anastomosis site.

14. The device of claim 1, wherein the distance between the first guide tube and the handle is configured to be reduced until the stop is positioned at or near the handle.

15. A method for introducing an implantable device into an intestine to protect an anastomosis site, the method comprising:
   introducing a distal end of a first guide tube of an introducer device through an anal orifice into the intestine to a position upstream of the anastomosis site, the first guide tube having the implantable device disposed therein, the introducer device comprising a second guide tube positioned proximal to the first guide tube and a stop between the first guide tube and the second guide tube, the stop having a diameter larger than that of the first guide tube and the second guide tube; and
   using a handle to reduce a distance between the first guide tube and the handle to release the implantable device out the distal end of the first guide tube at the position upstream of the anastomosis site for implanting the implantable device for protecting the anastomosis site.

16. The method of claim 15, further comprising applying and maintaining suction to the implantable device at the position upstream of the anastomosis site to anchor the implantable device within the intestine.

17. The method of claim 15, wherein the implantable device comprises a stent coupled to a sheath, and
   wherein the stent expands upon deployment from the distal end of the first guide tube to contact an intestine wall at the position for anchoring.

18. The method of claim 15, wherein using the handle comprises actuating an actuator at the handle to control longitudinal translation.

19. The method of claim 15, wherein reducing the distance between the first guide tube and the handle causes the second guide tube to move into the handle.

20. The method of claim 15, wherein releasing the implantable device comprises elastically deforming cut-out tabs at the distal end of the first guide tube to permit the implantable device to be deployed therethrough.

* * * * *